(12) United States Patent
Tachibana et al.

(10) Patent No.: US 10,697,004 B2
(45) Date of Patent: Jun. 30, 2020

(54) CLAMPING PROBE

(71) Applicant: Osaka City University, Osaka-shi, Osaka (JP)

(72) Inventors: Akira Tachibana, Osaka (JP); Toshizumi Tanabe, Osaka (JP)

(73) Assignee: Osaka City University, Osaka (JP)

( * ) Notice: Subject to any disclaimer, the term of this patent is extended or adjusted under 35 U.S.C. 154(b) by 0 days.

(21) Appl. No.: 15/524,656

(22) PCT Filed: Nov. 6, 2015

(86) PCT No.: PCT/JP2015/081403
§ 371 (c)(1),
(2) Date: May 5, 2017

(87) PCT Pub. No.: WO2016/072516
PCT Pub. Date: May 12, 2016

(65) Prior Publication Data
US 2017/0356033 A1 Dec. 14, 2017

(30) Foreign Application Priority Data
Nov. 6, 2014 (JP) .................................. 2014-226332

(51) Int. Cl.
*C12Q 1/6827* (2018.01)
*C12N 15/09* (2006.01)
(Continued)

(52) U.S. Cl.
CPC ........... *C12Q 1/6827* (2013.01); *C12N 15/09* (2013.01); *C12Q 1/68* (2013.01); *C12Q 1/6806* (2013.01);
(Continued)

(58) Field of Classification Search
CPC ..... C12Q 1/6867; C12N 15/09; G01N 33/574
See application file for complete search history.

(56) References Cited

U.S. PATENT DOCUMENTS 6,312,894 B1 11/2001 Hedgpeth et al.
9,297,036 B2 * 3/2016 Wang .................. C12Q 1/6837
(Continued)

FOREIGN PATENT DOCUMENTS

JP 2002-527040 8/2002
JP 2004-514427 5/2004
(Continued)

OTHER PUBLICATIONS

"Viruses", Wikipedia.com, accessed Nov. 24, 2012. (Year: 2012).*
(Continued)

*Primary Examiner* — Narayan K Bhat
(74) *Attorney, Agent, or Firm* — McCarter & English, LLP

(57) ABSTRACT

A method in which a mutant gene present in a gene pool mixedly with a large number of wild-type genes can be simply, inexpensively and sensitively detected is developed and provided. A clamping probe that is connected to a target nucleic acid molecule in two regions of first and second target nucleic acid complementary regions so that a wild-type target nucleic acid molecule and a mutant-type target nucleic acid molecule can be distinguished from each other depending on a difference in complementarity to these target nucleic acid molecules is provided.

17 Claims, 15 Drawing Sheets

Specification includes a Sequence Listing.

(51) Int. Cl.
| | |
|---|---|
| C12Q 1/68 | (2018.01) |
| G01N 33/574 | (2006.01) |
| C12Q 1/6806 | (2018.01) |
| C12Q 1/6809 | (2018.01) |
| C12Q 1/6811 | (2018.01) |
| C12Q 1/6851 | (2018.01) |
| C12Q 1/6883 | (2018.01) |

(52) U.S. Cl.
CPC .......... *C12Q 1/6809* (2013.01); *C12Q 1/6811* (2013.01); *C12Q 1/6851* (2013.01); *C12Q 1/6883* (2013.01); *G01N 33/574* (2013.01)

(56) References Cited

U.S. PATENT DOCUMENTS

| | | | | |
|---|---|---|---|---|
| 2004/0063906 | A1 | 4/2004 | Nielsen et al. | |
| 2004/0191801 | A1* | 9/2004 | Heeger | B82Y 15/00 435/6.12 |
| 2006/0286570 | A1* | 12/2006 | Rowlen | C12Q 1/6816 435/6.12 |
| 2007/0031829 | A1* | 2/2007 | Yasuno | C12Q 1/6886 435/6.12 |
| 2007/0042400 | A1* | 2/2007 | Choi | C12N 15/10 435/6.12 |
| 2007/0042419 | A1* | 2/2007 | Barany | C12Q 1/6813 435/6.12 |
| 2012/0014977 | A1* | 1/2012 | Furihata | C07K 14/4748 424/185.1 |
| 2012/0252012 | A1* | 10/2012 | Armougom | C12Q 1/689 435/6.11 |
| 2013/0005589 | A1 | 1/2013 | Matsumoto et al. | |
| 2018/0057868 | A1* | 3/2018 | Walder | C12Q 1/6869 |

FOREIGN PATENT DOCUMENTS

| | | |
|---|---|---|
| JP | 2011049343 | 4/2011 |
| JP | 2013-150631 | 8/2013 |
| WO | 2007046158 | 4/2007 |
| WO | WO 2015/068957 | 5/2015 |

OTHER PUBLICATIONS

"How many species of bacteria are there", wisegeek.com; accessed Jan. 21, 2014. (Year: 2014).*
"Fungi," Wikipedia.com; accessed Jun. 3, 2013. (Year: 2013).*
"Plant," Wikipedia.com; accessed Aug. 28, 2015. (Year: 2015).*
"Mammal," Wikipedia.com; accessed Sep. 22, 2011. (Year: 2011).*
"Murinae," Wikipedia.com, accessed Mar. 18, 2013. (Year: 2013).*
"Fish," Wikipedia.com, accessed Nov. 2, 2014. (Year: 2014).*
"Archaea," Wikipedia.com, accessed May 11, 2016. (Year: 2016).*
"Algae," Wikipedia.com, accessed Mar. 4, 2016. (Year: 2016).*
"Protozoa," Wikipedia.com, accessed May 11, 2016. (Year: 2016).*
"List of sequenced bacterial genomes", Wikipedia.com; accessed Jan. 24, 2014. (Year: 2014).*
Sharon Begley, "Psst, the human genome was never completely sequenced", STATNews.com, Jun. 20, 2017. (Year: 2017).*
Tachibana et al, LidNA, a novel miRNA inhibitor constructed with unmodified DNA, 2012, FEBS Letters, 586, 1529-1532 (Year: 2012).*
Hynes, Nancy E., et al., "ERBB Receptors and Cancer: The Complexity of Targeted Inhibitors", Nature Reviews Cancer, May 2005, vol. 5, pp. 341-354.
Spano, J.P., et al., "Impact of EGFR Expression on Colorectal Cancer Patient Prognosis and Survival", Annals of Oncology, 2005, vol. 16, pp. 102-108
Lievre, Astrid, et al., "KRAS Mutations as an Independent Prognostic Factor in Patients with Advanced Colorectal Cancer Treated with Cetuximab", Journal of Clinical Oncology, Jan. 20, 2008, vol. 26, No. 3, pp. 374-379.
Lievre, Astrid, et al., "KRAS Mutation Status is Predictive of Response to Cetuximab Therapy in Colorectal Cancer", The Journal of Cancer Research, Apr. 15, 2006, vol. 66, No. 8, pp. 3992-3995.
Daicho-gan Kanja, Guidelines for RAS gene (KRAS/NRAS Gene) Mutation Testing in Colon Cancer Patients, Apr. 2014, Japanese Society of Medical Oncology, 2014, pp. 1-21 (with partial English Translation).
Huang, Qing, et al., "High Sensitive Mutation Analysis on KRAS2 Gene Using LNA-DNA Chimeras as PCR Amplification Blockers of Wiki-Type Alleles", Molecular and Cellular Probes, 2010, vol. 24, pp. 376-380.
Oh, Ji Eun, et al., "Detection of Low-Level KRAS Mutations Using PNA-Mediated Asymmetric PCR Clamping and Melting Curve Analysis with Unlabeled Probes", Journal of Molecular Diagnostics, Jul. 2010, vol. 12, No. 4, pp. 418-424.
Dahse, Regine, et al., "PCR-based Testing for Therapy-related EGFR Mutations in Patients with Non-Small Cell Lung Cancer", AntiCancer Research, 2008, vol. 28, pp. 2265-2270.
International Search Report based on International Application No. PCT/JP2015/081403 dated Jan. 26, 2016—4 Pages.
Supplemental European Search Report relating to co-pending European Application No. 15857156.2, dated Mar. 16, 2018—9 Pages.
Luo, Ji-Dung, et al., "Detection of rare mutant K-ras DNA in a single-tube reaction using peptide nucleic acid as both PCR clamp and sensor probe", Nucleic Acids Research, 2006, vol. 34, No. 2, pp. 1-7.
Bikard, David, et al., "Folded DNA in Action: Hairpin Formation and Biological Functions in Prokaryotes", Microbiology and Molecular Biology Reviews, Dec. 2010, vol. 74, No. 4, pp. 570-588.

* cited by examiner

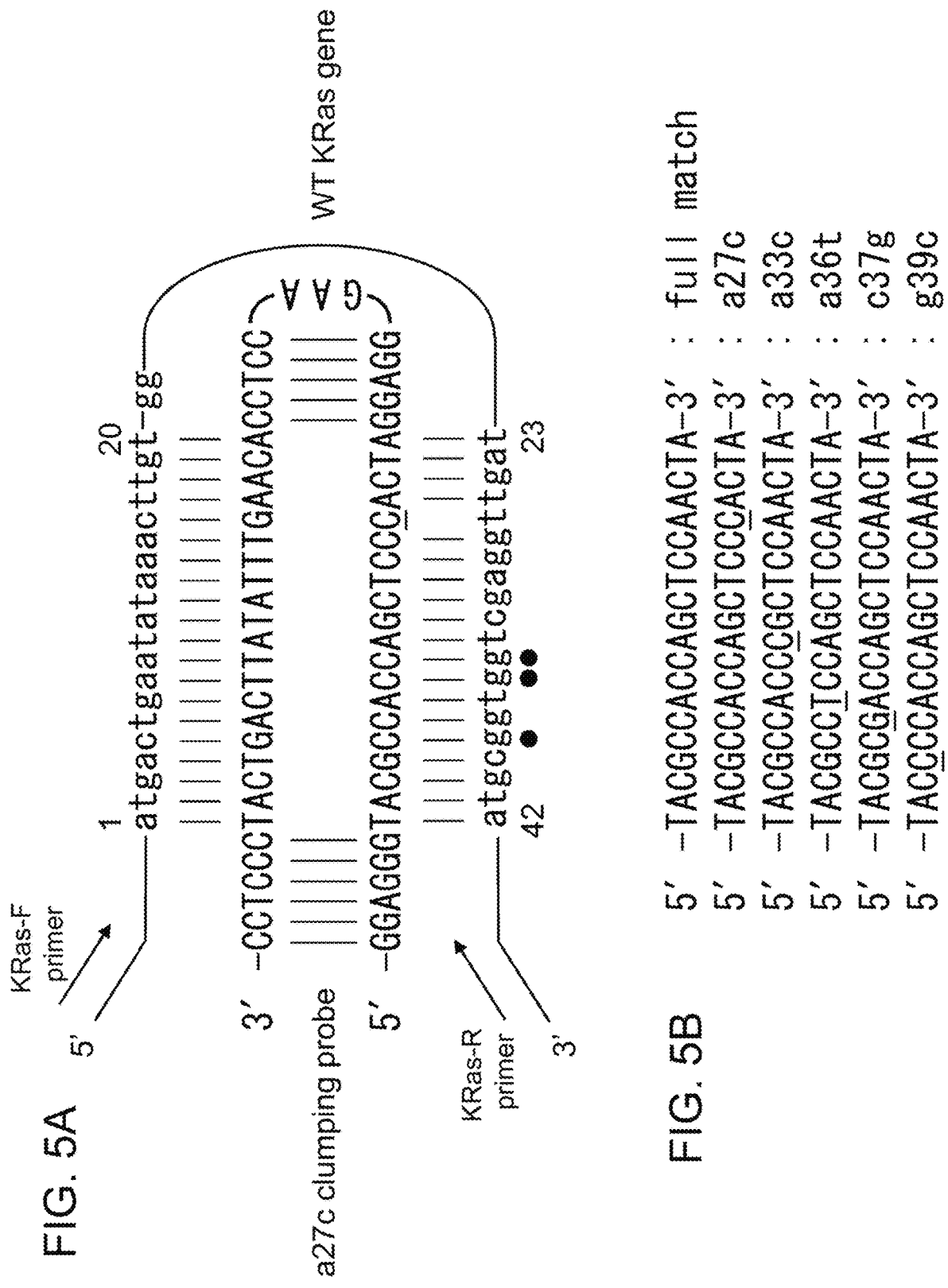

CLAMPING PROBE

RELATED APPLICATIONS

This application is a national stage application filed under 35 USC 371 of PCT/JP2015/081403, filed Nov. 6, 2015, which claims the benefit of Japanese Patent Application No. 2014-226332, filed Nov. 6, 2014, all of which is incorporated herein, in its entirety, by reference.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 11924400119.txt. The size of the text file is 9 KB, and the text file was created on May 2, 2017.

TECHNICAL FIELD

The present invention relates to a clamping probe capable of simply, inexpensively and sensitively detecting known mutation in a target nucleic acid molecule, and a method for detecting the known mutation in a target nucleic acid molecule using the same.

BACKGROUND ART

Epidermal growth factor receptor (EGFR), which is a transmembrane tyrosine kinase-type receptor, forms a dimer by binding to epidermal growth factor (EGF) or the like, so as to transmit a signal downstream by autophosphorylation activity. This signaling pathway via the EGFR functions, in a normal cell, in control of cell differentiation, cell growth and the like. If hyperactivity occurs in this signaling pathway due to some abnormality, however, the control mechanism for the cell growth and the like fails, which is regarded to cause induction, growth, metastasis, invasion and the like of cancer (Non Patent Literature 1). For example, overexpression of the EGFR is found in about 80% of colorectal cancer (Non Patent Literature 2).

Therefore, as an antibody drug against colorectal cancer based on the aforementioned mechanism, an anti-EGFR antibody drug has recently been developed. For example, cetuximab and panitumumab are anti-EGFR monoclonal antibody drugs for inhibiting the cell growth as a ligand-EGFR binding inhibitor.

It has been revealed, however, that the effect of the anti-EGFR antibody drug such as cetuximab is weak in a patient with KRas gene mutation (Non Patent Literatures 3 and 4). The KRas gene is one of isoforms of the ras gene known as an oncogene. KRAS encoded by this gene activates a signal cascade as a low molecular weight guanosine triphosphate (GTP)-binding protein to transmit downstream a cell growth signal from the epidermal growth factor receptor (EGFR). If a specific position of the KRas gene mutates, the function of the KRAS as GTPase is degraded, and the KRAS becomes a constitutively activated form for continuously transmitting the signal downstream. This excessive signaling is believed to impart a negative effect to the anti-EGFR antibody drug. Actually, in many patients affected with colorectal cancer which tends to become severe, in which the therapeutic effect of the anti-EGFR antibody drug is weak, it has been revealed that mutation is found in codon 12 or codon 13 of the KRas gene (Non Patent Literature 5). Accordingly, it is very significant in selecting a treatment for a patient to precedently predict an effect of the antibody drug by analyzing mutation in KRas gene in a biological sample obtained from the subject before administering the anti-EGFR antibody drug.

However, a pathological sample used in mutation analysis generally contains not only tumor cells but also a large number of normal cells. In particular, in a pathological sample obtained from a subject having early cancer, most of the cells are normal cells and merely a small number of tumor cells having mutant-type KRas gene are mixedly present. Accordingly, there is a serious problem that target mutant-type KRas gene cannot be detected by a usual nucleic acid amplification method because wild-type KRas gene is priorly amplified. Therefore, a technique for simply and sensitively detecting mutant-type KRas gene in the presence of an excessive amount of wild-type KRas gene or a genotype diagnostic agent used as a companion diagnostic agent for precedently determining the efficacy of an anti-cancer drug is desired.

Therefore, a nucleic acid amplification method for selectively and efficiently amplifying a mutant gene by inhibiting the amplification of a wild-type gene using a nucleic acid analogue and the like has been studied. For example, a method, in which a BNA/LNA (Bridged Nucleic Acid/Locked Nucleic Acid) probe for inhibiting the amplification of a wild-type gene is mixedly used in amplifying a known mutation site by PCR or the like to determine mutation contained in the amplified PCR product by an invader method and the like, has been developed (Non Patent Literature 6). Besides, Patent Literature 1 discloses a method for applying, to PCR clamping, a minor groove binder (MGB)-oligonucleotide conjugate having high affinity with a DNA. Furthermore, Patent Literature 2 and Non Patent Literature 7 describe PCR clamping using PNA (Peptide Nucleic Acid).

Nucleic acid analogs such as BNA/LNA and PNA are, however, expensive, and in addition, there still remains a problem that a combination of the nucleic acid amplification method and the invader method is complicated. Furthermore, all the aforementioned methods still have a problem that the presence of a mutant gene cannot be determined at normal temperature.

CITATION LIST

Patent Literature

Patent Literature 1: JP Patent Publication (Kohyo) No. 2002-527040
Patent Literature 2: JP Patent Publication (Kohyo) No. 2004-514427

Non Patent Literature

Non Patent Literature 1: Hynes N. E. & Lane H. A., 2005, Nat Rev Cancer, 5: 341-354
Non Patent Literature 2: Spano J. P. et al., 2005, Ann Oncol, 16: 102-108
Non Patent Literature 3: Lievre A., et al., 2008, J Clin Oncol., 26(3): 374-9
Non Patent Literature 4: Lievre A., et al., 2006, Cancer Res. 66(8): 3992-5
Non Patent Literature 5: Daicho-gan Kanja niokeru KRAS idenshiheni no Sokutei nikansuru Gaidansu (Guidance for Measurement of KRAS Gene Mutation in Colorectal Cancer Patient) (2nd edition), (edited by) KRAS Gene Mutation Examination Committee of Japanese Society of Medical Oncology, 2014

Non Patent Literature 6: Huang Q., et al., 2010, Mol. Cell. Probes, 24: 376-380

Non Patent Literature 7: Oh J. E., et al., 2010, Journal of Mol. Diag., 12: 418-424

SUMMARY OF INVENTION

Technical Problem

An object of the present invention is to develop and provide a method capable of simply, inexpensively and sensitively detecting a mutant gene present in a gene pool mixedly with a large number of wild-type genes.

Solution to Problem

In order to solve the aforementioned problem, the present inventors have developed a clamping probe constituted by a naturally occurring nucleic acid without a non-naturally occurring nucleic acid such as a nucleic acid analog. The present invention is based on the result of this development, and provides the following:

(1) A clamping probe for use for detecting known mutation in a target nucleic acid molecule caused by substitution, deletion or addition of one or several bases, the clamping probe comprising a single-stranded nucleic acid molecule comprising a first target nucleic acid complementary region, a second target nucleic acid complementary region, a hairpin region and a double-stranded region, one of a combination of a 3'-end of the first target nucleic acid complementary region and a 5'-end of the second target nucleic acid complementary region and a combination of a 3'-end of the second target nucleic acid complementary region and a 5'-end of the first target nucleic acid complementary region being connected to the hairpin region, and the other combination being connected to the double-stranded region, wherein the first target nucleic acid complementary region consists of a nucleotide sequence complementary to a nucleotide sequence of a first target nucleic acid region, the first target nucleic acid region consists of continuous 15 to 30 bases including a site of the known mutation in a wild-type target nucleic acid molecule, the second target nucleic acid complementary region consists of a nucleotide sequence complementary to a nucleotide sequence of a second target nucleic acid region, the second target nucleic acid region consists of 15 to 30 bases flanking on a 5'-end side or a 3'-end side of the first target nucleic acid region in the target nucleic acid molecule, the hairpin region comprises: a double-stranded moiety consisting of mutually complementary nucleotide sequences each of 3 to 10 bases; and a single-stranded moiety consisting of a nucleotide sequence of 3 to 10 bases connecting any combination of a 5'-end and a 3'-end of the double-stranded moiety, and the double-stranded region consists of mutually complementary nucleotide sequences each of 3 to 10 bases.

(2) The clamping probe according to (1), wherein the first target nucleic acid complementary region comprises a mismatch site of 1 to 3 bases not complementary to the nucleotide sequence of the first target nucleic acid region.

(3) The clamping probe according to (1) or (2), comprising a spacer region consisting of a nucleotide sequence of 1 to 5 bases linking the first target nucleic acid complementary region and/or the second target nucleic acid complementary region to the hairpin region, and/or the first target nucleic acid complementary region and/or the second target nucleic acid complementary region to the double-stranded region.

(4) The clamping probe according to any one of (1) to (3), wherein a G-quartet region is connected to at least one of a free 5'-end and a free 3'-end of the double-stranded region.

(5) The clamping probe according to any one of (1) to (4), wherein the target nucleic acid molecule is KRas gene represented by SEQ ID NO: 1.

(6) The clamping probe according to (5), wherein the mutation is substitution mutation in at least one base selected from the group consisting of positions 34, 35 and 38.

(7) The clamping probe according to any one of (1) to (4), wherein the target nucleic acid molecule is EGFR gene represented by SEQ ID NO: 2.

(8) The clamping probe according to (7), wherein the mutation is substitution mutation in any one base selected from the group consisting of positions 2115, 2573 and 2582.

(9) A method for detecting presence of known mutation in a target nucleic acid molecule, comprising: mixing a nucleic acid sample containing the target nucleic acid molecule with the clamping probe according to any one of (1) to (4) for binding the target nucleic acid molecule and the clamping probe to each other; and detecting mutation in the target nucleic acid molecule based on a difference in binding force between the target nucleic acid molecule and the clamping probe caused depending on the presence of the mutation in the target nucleic acid molecule.

(10) The method according to (9), wherein detection based on the difference in the binding force is detection based on an amount difference of an amplified product obtained by a nucleic acid amplification method, and a region of the target nucleic acid molecule comprising the first target nucleic acid region and the second target nucleic acid region is amplified by the nucleic acid amplification method.

(11) The method according to (9), wherein the detection based on the difference in the binding force is detection based on a molecular sieve.

(12) The method according to any one of (9) to (11), wherein the target nucleic acid molecule is KRas gene represented by SEQ ID NO: 1.

(13) The method according to (12), wherein the mutation is substitution mutation in at least one base selected from the group consisting of positions 34, 35 and 38.

(14) The method according to any one of (9) to (11), wherein the target nucleic acid molecule is EGFR gene represented by SEQ ID NO: 2.

(15) The method according to (14), wherein the mutation is substitution mutation in any one base selected from the group consisting of positions 2115, 2573 and 2582.

(16) A method for determining whether a subject is affected with colorectal cancer, comprising: preparing a nucleic acid sample from a biological sample obtained from the subject; detecting presence of known mutation in the KRas gene of (12) or (13) by using the obtained nucleic acid sample; and determining that the subject is liable to be affected with colorectal cancer if the KRas gene having the mutation is detected in the nucleic acid sample.

(17) A method for determining whether a subject is affected with non-small cell lung cancer, comprising: preparing a nucleic acid sample from a biological sample obtained from the subject; detecting presence of known mutation in the EGFR gene of (14) or (15) by using the obtained nucleic acid sample; and determining that the subject is liable to be affected with non-small cell lung cancer if the EGFR gene having the mutation is detected in the nucleic acid sample.

The present application encompasses the contents of JP Patent Application No. 2014-226332 based on which the present application claims the benefit of priority.

Advantageous Effects of Invention

The clamping probe of the present invention can sensitively detect a mutant gene present in a gene pool mixedly with a large number of wild-type genes.

The clamping probe of the present invention is constituted by a naturally occurring nucleic acid, mainly a DNA, and hence can be inexpensively provided.

BRIEF DESCRIPTION OF DRAWINGS

FIGS. 4A and 4B show diamond-type linking, and FIGS. 4C and 4D show a parallel-type linking.

FIG. 5A shows the binding between a27c clamping probe for a KRas gene (capital letters) and wild-type KRas gene (small letters) used in a nucleic acid amplification method. A black circle corresponds to a site where mutation is often found in the KRas gene (i.e., a known mutation site). FIG. 5B shows nucleotide sequences of first target nucleic acid complementary regions of the clamping probe. The wording "full match" shown in the figure means a nucleotide sequence of the first target nucleic acid complementary region in the full match-type clamping probe whose nucleotide sequence is completely complementary to a nucleotide sequence of the first target nucleic acid region of wild-type KRas gene, and sequences shown as "a27c", "a33c", "a36t", "c37g" and "g39c" are nucleotide sequences of the first target nucleic acid complementary regions of mismatch-type clamping probes. Each underlined base in the mismatch-type clamping probe corresponds to a base where a mismatch site is introduced.

FIG. 8 are comparison diagram of the amount of an amplified product obtained by using a parallel-type or diamond-type clamping probe with wild-type (W) or mutant-type (M) KRas gene used as a template.

FIG. 9 are diagrams of melting curve analysis of a clamping probe and KRas gene.

FIG. 10 are comparison diagram of the amount of an amplified product obtained through shuttle PCR using a full match-type clamping probe with wild-type (W) or mutant-type (M) KRas gene used as a template.

FIG. 11 are comparison diagrams of the amount of an amplified product obtained through the shuttle PCR using the full match-type clamping probe and using a primer pair having a larger Tm value than a primer pair used in FIGS. 10A and 10B with wild-type (WT) or mutant-type (Mutant) KRas gene used as a template.

DESCRIPTION OF EMBODIMENTS

Figure 1:
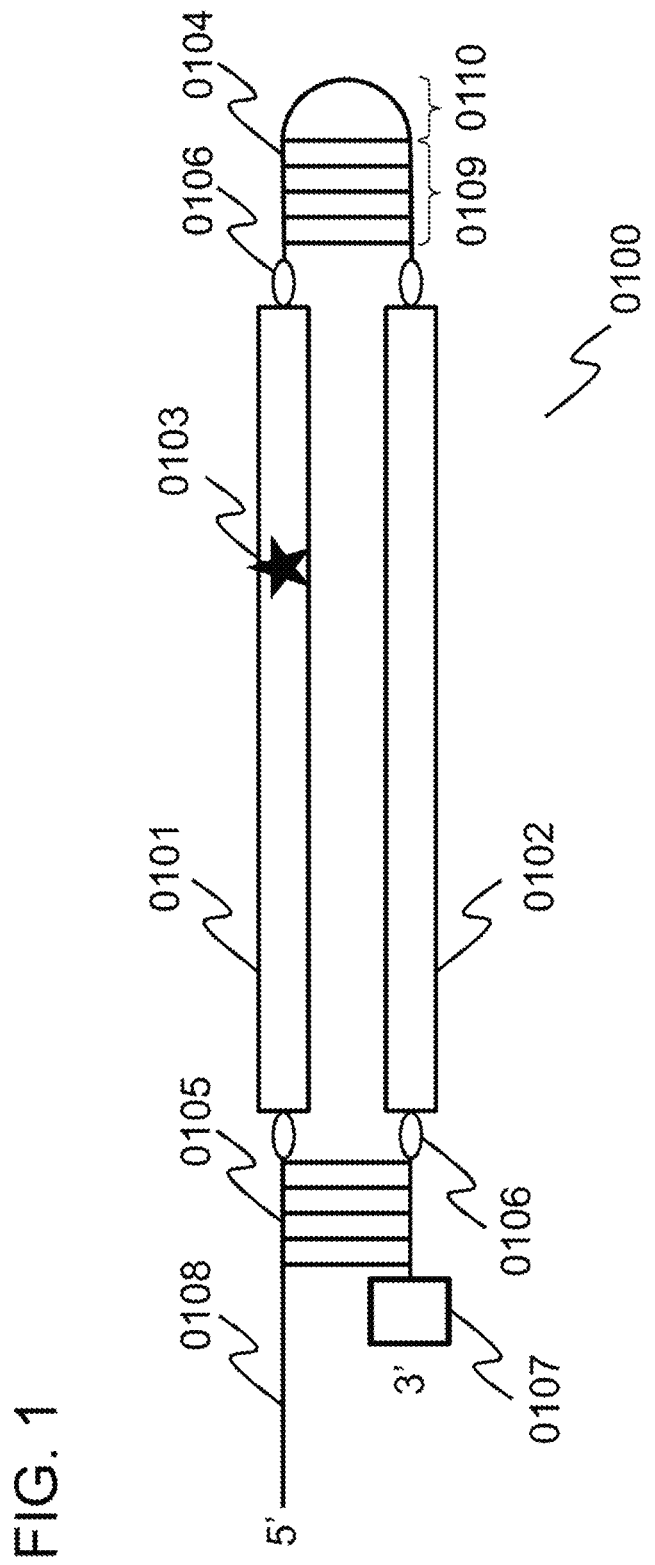
FIG. 1 is a diagram showing a basic structure of a clamping probe of the present invention. Respective portions showing reference numerals are described in "1-3. Structure" as described below.

Aspects of the present invention are specifically described below.

1. Clamping Probe

1-1. Outline

A first aspect of the present invention is a clamping probe. The clamping probe of the present invention is a single-stranded nucleic acid probe for detecting known mutation that may be contained in a target nucleic acid molecule.

By using the clamping probe of the present invention, for example, a specific mutant gene present mixedly with a large number of wild-type genes can be simply and sensitively detected.

Additionally, the clamping probe of the present invention is also applicable to a method for detecting a well-known mutation sites, such as the invader method (Huang Q., et al., 2010, Mol. Cell. Probes, 24: 376-380), and by combining a method for detecting the presence of known mutation in a target nucleic acid molecule using a clamping probe described below as a second aspect and the method for detecting a well-known mutation sites, a specific mutant gene present mixedly with wild-type genes can be more accurately detected.

1-2. Definitions

Definitions of terms used herein are described below.

The term "nucleic acid" refers to a naturally occurring nucleic acid, a non-naturally occurring nucleic acid and/or a nucleic acid analog.

The term "naturally occurring nucleic acid" refers to a biopolymer present in nature and containing nucleotides as constituting units linked to one another via phosphodiester bonds. In general, it corresponds to an RNA containing connected ribonucleotides each having any one of bases of adenine (A), guanine (G), cytosine (C) and uracil (U), or a DNA containing connected deoxyribonucleotides each having any one of bases of adenine, guanine, cytosine and thymine (T).

The term "non-naturally occurring nucleic acid" refers to a nucleic acid molecule wholly or partly containing a non-naturally occurring nucleotide. The term "non-naturally occurring nucleotide" refers to a nucleotide that is not present in nature but is artificially constructed or artificially chemically modified, and has a property and/or a structure similar to that of the nucleotide present in nature, or a nucleotide containing a nucleoside or a base having a property and/or a structure similar to a nucleoside or a base present in nature. Examples include an abasic nucleoside, an arabinonucleoside, 2'-deoxyuridine, α-deoxyribonucleoside, β-L-deoxyribonucleoside, and a nucleoside having another sugar modification. Another example includes a nucleoside having sugar modification with substituted pentose (2'-O-methyl ribose, 2'-deoxy-2'fluoro ribose, 3'-O-methyl ribose or 1',2'-deoxyribose), arabinose, substituted arabinose sugar, substituted hexose or α-anomer. Besides, the non-naturally occurring nucleotide comprises a nucleotide containing an artificially constructed base analog or an artificially chemically modified base (modified base). Examples of the "base analog" include a 2-oxo(1H)-pyridine-3-yl group, a 5-position substituted-2-oxo(1H)-pyridine-3-yl group, a 2-amino-6-(2-thiazolyl)purine-9-yl group, a 2-amino-6-(2-thiazolyl)purine-9-yl group and a 2-amino-6-(2-oxazolyl)purine-9-yl group. Examples of the "modified base" include modified pyrimidine (such as 5-hydroxycytosine, 5-fluorouracil or 4-thiouracil), modified purine (such as 6-methyladenine or 6-thioguanosine) and other heterocyclic bases. Examples also include chemically modified nucleic acids and nucleic acid analogs such as methyl phosphonate-type DNA/RNA, phosphorothioate-type DNA/RNA, phosphoramidate-type DNA/RNA and 2'-O-methyl-type DNA/RNA.

The term "nucleic acid analog" refers to an artificially constructed compound having a structure and/or a property similar to that of a naturally occurring nucleic acid. Examples include PNA, PHONA (peptide nucleic acid having a phosphate group), BNA/LNA and morpholino nucleic acid.

The nucleic acid may be labeled with a nucleic acid marker at a phosphoric acid group, a sugar and or a base thereof if necessary. As the nucleic acid marker, any of substances known in this art can be used. Examples include radioisotopes (such as $^{32}P$, $^{3}H$ and $^{14}C$), DIG, biotin, fluorescent dyes (such as FITC, Texas, Cy3, Cy5, Cy7, FAM, HEX, VIC, JOE, Rox, TET, Bodipy 493, NBD and TAMRA) and luminescent substances (such as acridinium ester).

The term "target nucleic acid molecule" refers to a single-stranded nucleic acid molecule corresponding to a target for detecting known mutation using the clamping probe of the present invention. In principle, the target nucleic acid molecule is constituted by a naturally occurring nucleic acid, and specific examples include a gene, an RNA molecule (including an mRNA precursor, a mature mRNA and a non-coding RNA) corresponding to a transcript of the gene, a chromosome and fragments thereof. Here, the term "non-coding RNA" refers to an RNA not encoding a protein but having various functions by itself. It corresponds to, for example, a transfer RNA (tRNA), a ribosome RNA (rRNA), a small nuclear RNA (snRNA), a small nucleolar RNA (snoRNA), a micro-RNA (miRNA; including a pre-miRNA) or the like. Incidentally, if a target nucleic acid molecule is a wild-type gene not having mutation described below or a transcript thereof, it is herein designated particularly as a "wild-type target nucleic acid molecule", and a counterpart of the wild-type gene, which has a mutation, or a transcript thereof, is called as a "mutant-type target nucleic acid molecule".

The term "mutation" refers to physical or structural change of a nucleotide sequence caused in a wild-type gene, and change of a transcript (RNA) or a translation product (protein) derived therefrom.

The term "wild-type gene" refers to an allele that is most abundantly present in an allele population of the same type of genes in nature, and a protein or a non-coding RNA encoded thereby has the original function. On the other hand, as a term corresponding to a counterpart of the wild-type gene, which has a mutation, an allele having the mutation in an allele population of the same type of genes is designated as a "mutant gene".

Examples of the mutation include substitution, deletion and addition of one or plural bases.

The term "substitution" refers to mutation in which one or plural, preferably one to three, and more preferably one or two bases are replaced with other bases in a wild-type gene or the like. An example includes point mutation in which one base in a position of a nucleotide sequence is replaced when compared with a nucleotide sequence of a wild-type gene or the like. As the point mutation, transition mutation corresponding to substitution between purines or pyrimidines and transversion mutation corresponding to substitution between a purine and a pyrimidine are known, and the point mutation may be either of these mutations. Besides, the point mutation includes both congenital mutation and acquired mutation. Furthermore, as the point mutation, missense mutation causing amino acid substitution, nonsense mutation causing a stop codon, silent mutation causing substitution with a degenerate codon and not causing amino acid substitution, and mutation in a splice site are known, but the point mutation is not especially limited. The point mutation is preferably missense mutation, nonsense mutation or mutation in a splice site.

The term "deletion" refers to mutation in which one or plural bases are deleted from a wild-type gene or the like. The number and the positions of deleted bases are not especially limited. It may be either deletion of 3n+1 or 3n+2 continuous bases (wherein "n" is an integer) causing frameshift mutation due to a shift in reading frame or deletion of 3n continuous bases causing deletion of several amino acids.

The term "addition" refers to mutation in which one or plural bases are inserted in a nucleotide sequence of a wild-type gene or the like. The insertion position of the bases is not especially limited. For example, the base(s) may be inserted into either or both of an exon and an intron. Preferably, the base(s) are inserted into an exon. If the base(s) are inserted into an exon, 3n+1 or 3n+2 bases causing frameshift mutation may be inserted, or 3n bases causing addition of several amino acids may be inserted.

The term "plural" refers to, for example, 2 to 20, 2 to 15, 2 to 10, 2 to 7, 2 to 5, 2 to 4, or 2 to 3.

The term "known mutation" refers to known mutation that can be present in a specific position of a target nucleic acid molecule. The specific position refers to a prescribed position in the target nucleic acid molecule. The mutation may be any of substitution, deletion and addition of one or plural bases. For example, in human KRas gene consisting of a nucleotide sequence represented by SEQ ID NO: 1, examples of the known mutations include g34a (which means point mutation of substitution of g with a in position 34 of wild-type KRas gene assuming that "a" of start codon "atg" is in position 1; the same applies hereinafter) (G12S: which means substitution of glycine in position 12 with serine in an amino acid sequence of wild-type KRAS; the same applies hereinafter), g34c (G12R), g34t (G12C), g35a (G12D), g35c (G12A), g35t (G12V) and g38a (G13D), which cause amino acid substitution in positions 12 and 13 known to make colorectal cancer severe (Martinetti D., et al., 2014, Diagn Pathol., 9(1): 187). Alternatively, in human EGFR gene consisting of a nucleotide sequence represented by SEQ ID NO: 2, examples of the known mutations include g2115t, g2155a, t2573g, t2582a, g2235Δc2249(15) (which means mutation of deletion of 15 bases from g in position 2235 to c in position 2249; the same applies hereinafter), g2236Δa2250(15), t2240Δa2251(12), t2240Δc2257(16), t2239Δa2247(9) and a2238Δc2255(18) known to cause non-small cell lung cancer (NSCLC) (Paez G. J., et al., 2004, Science, 304: 1497-1500).

1-3. Structure

Figure 3:
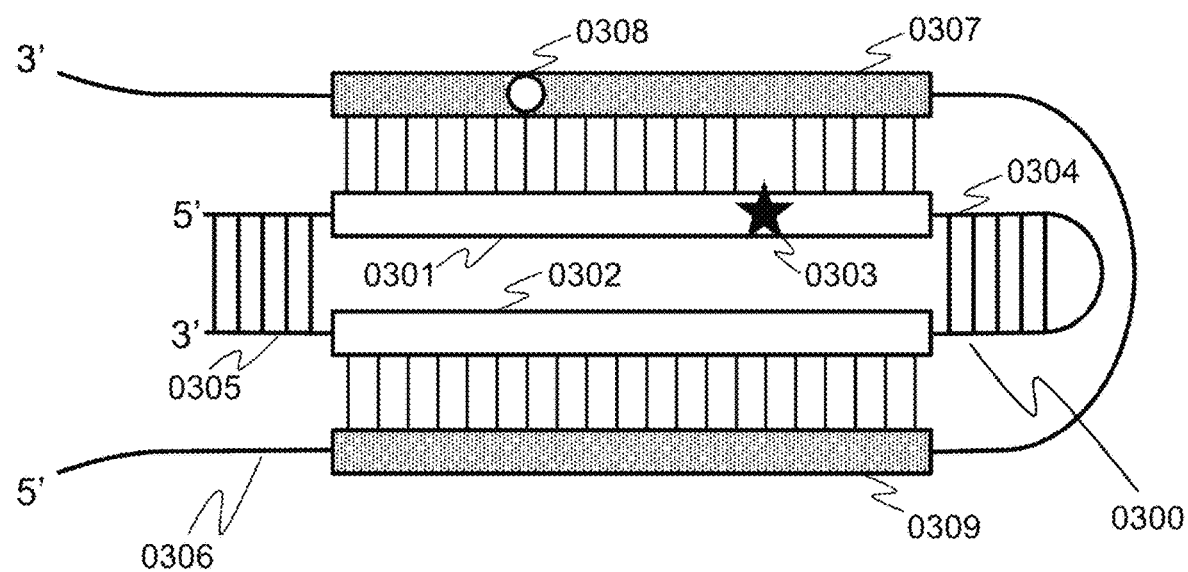
FIG. 3 is a diagram showing a binding relationship between the clamping probe of the present invention and a target nucleic acid molecule. Respective portions shown by reference numerals in this figure are described in "1-3. Structure" as described below.

Herein, the term "clamping probe" refers to a single-stranded nucleic acid molecule having a basic structure shown in FIG. 1, having sequence specificity to a target nucleic acid molecule and having a high dissociation temperature (Tm). A binding relationship between the clamping probe of the present invention and a target nucleic acid molecule is shown in FIG. 3.

The clamping probe (0100 or 0300) of the present invention contains, as essential components, a first target nucleic acid complementary region (0101 or 0301), a second target nucleic acid complementary region (0102 or 0302), a hairpin region (0104 or 0304) and a double-stranded region (0105 or 0305). Besides, the clamping probe of the present invention contains, as selective components, a mismatch site (0103 or 0303), a spacer region (0106), a G-quartet region (0107) and a flanking region (0108) in addition to the aforementioned essential components.

The respective components are specifically described below.

(1) First Target Nucleic Acid Complementary Region

The "first target nucleic acid complementary region" (0101 or 0301) is a region consisting of a nucleotide sequence complementary to a nucleotide sequence of a first target nucleic acid region (0307) of a target nucleic acid molecule (0306).

The "first target nucleic acid region" (0307) refers to a region that is present in a wild-type target nucleic acid molecule and consists of a nucleotide sequence of continuous 15 to 30 bases, preferably 15 to 25 bases or 15 to 20 bases containing a known mutation site (0308) to be detected by the clamping probe.

The "known mutation site" (0308) refers to a site where known mutation can be present in the target nucleic acid molecule. A wild-type target nucleic acid molecule has, however, no mutation in the known mutation site but has a wild-type base. If plural known mutation sites are simultaneously present in continuous 20 bases, the first target nucleic acid region may contain one or more known mutations. Incidentally, a site complementary to the known mutation site of the first target nucleic acid region in the first target nucleic acid complementary region is herein designated as a "mutation complementary site".

The target nucleic acid molecule which is source of the first target nucleic acid region is a wild-type target nucleic acid molecule in principle, but may be a mutant-type target nucleic acid molecule. Either may be appropriately selected in accordance with use of the clamping probe. If the clamping probe is used, in a gene pool mixedly containing a plurality of different target nucleic acid molecules, for example, a wild-type target nucleic acid molecule and a mutant-type target nucleic acid molecule, for detecting either of the molecules, the target nucleic acid molecule forming a larger subpopulation in the population of the gene pool may be selected. For example, if a mutant-type target nucleic acid molecule is desired to detect in a gene pool in which a small number of mutant-type target nucleic acid molecules are present mixedly with a large number of wild-type target nucleic acid molecules, a nucleotide sequence derived from the wild-type target nucleic acid molecule is selected as the first target nucleic acid region.

The first target nucleic acid complementary region consists of the nucleotide sequence complementary to the nucleotide sequence of the first target nucleic acid region, and hence, the nucleotide sequence and the base length thereof are inevitably determined excluding a mismatch site described later.

The first target nucleic acid complementary region recognizes the target nucleic acid molecule through the nucleotide sequence complementary to the nucleotide sequence of the first target nucleic acid region, and binds to the first target nucleic acid region.

(2) Second Target Nucleic Acid Complementary Region

The "second target nucleic acid complementary region" (0102 or 0302) is a region consisting of a nucleotide sequence complementary to a nucleotide sequence of a second target nucleic acid region (0309) of the target nucleic acid molecule.

Herein, the "second target nucleic acid region" (0309) consists of 15 to 30 bases, preferably 15 to 25 bases or 15 to 20 bases present in the target nucleic acid molecule and flanking on the 5'-end or the 3'-end of the first target nucleic acid region.

The term "flanking on" refers to placement in an adjacent position or a very close position with 1 to 5 bases, preferably 1 to 3 bases sandwiched therebetween.

The second target nucleic acid region need not have the same base length as the first target nucleic acid region. For example, the first target nucleic acid region may have a base length of 15 bases while the second target nucleic acid region has a base length of 20 bases.

The second target nucleic acid region is a region not containing a known mutation site in principle, but can contain a known mutation site. In this case, the second target nucleic acid region is the same in the structure as the first target nucleic acid region except that it flanks to the first target nucleic acid region.

The second target nucleic acid complementary region consists of a nucleotide sequence complementary to the nucleotide sequence of the second target nucleic acid region, and hence, the nucleotide sequence and the base length thereof are inevitably determined.

The second target nucleic acid complementary region recognizes the target nucleic acid molecule through the nucleotide sequence complementary to the nucleotide sequence of the second target nucleic acid region, and binds to the second target nucleic acid region.

(3) Mismatch Site

The "mismatch cite" (0103 or 0303) is a site, in the first target nucleic acid complementary region, where a base not complementary to the nucleotide sequence of the first target nucleic acid region of the wild-type target nucleic acid molecule is intentionally inserted.

As described above, the nucleotide sequence of the first target nucleic acid complementary region is constituted by a completely complementary (full match) nucleotide sequence to the nucleotide sequence of the first target nucleic acid region of the wild-type target nucleic acid molecule in principle. Some bases of the mismatch site are, however, constituted not to be able to pair with corresponding bases of the first target nucleic acid region. This is for purposes of appropriately weakening the binding property between the wild-type target nucleic acid molecule and the first target nucleic acid complementary region by introducing a non-complementary site, and further of causing a difference in binding stability of the clamping probe between the wild-type target nucleic acid molecule and the mutant-type target nucleic acid molecule described later.

The mismatch site may comprise an arbitrary base of the first target nucleic acid complementary region excluding the base of the mutation complementary site. Incidentally, the mutation complementary site cannot pair with the known mutation site of the mutant-type target nucleic acid molecule because it is complementary to the known mutation site of the wild-type target nucleic acid molecule. Therefore, the mutation complementary site is mismatched even without introducing a mismatch site into the mutant-type target nucleic acid molecule. In other words, while the wild-type target molecule cannot be complementary to merely the mismatch site of the first target nucleic acid region of the clamping probe, the mutant-type target nucleic acid molecule cannot be complementary not only to the mismatch site but also to the mutation complementary site. Therefore, its binding to the clamping probe is weaker than that of the wild-type target molecule. The mismatch site is useful for causing a difference in the binding stability of the clamping probe between the wild-type target nucleic acid molecule and the mutant-type target nucleic acid molecule.

The number of mismatch sites is 1 to 3, and preferably 1 or 2. If a plurality of mismatch sites are contained, they may be in positions continuous to or spaced from each other in the first target nucleic acid complementary region.

(4) Hairpin Region

The "hairpin region" (0104 or 0304) is a region linking the first target nucleic acid complementary region and the second target nucleic acid complementary region. It has a structure, as shown in FIG. 1, comprising a double-stranded moiety (0109) corresponding to a stem and a single-stranded moiety (0110) corresponding to a loop.

The "double-stranded moiety" (0109) consists of double strands having mutually complementary nucleotide sequences each of 3 to 10 bases, preferably 4 to 9 bases, 4 to 8 bases, 5 to 7 bases, or 5 or 6 bases. The nucleotide sequences constituting the double-stranded moiety are not especially limited, and are preferably nucleotide sequences having a large GC content.

The "single-stranded moiety" (0110) consists of a single strand having a nucleotide sequence of 3 to 10 bases, preferably 3 to 9 bases, 3 to 6 bases or 3 to 5 bases. The nucleotide sequence constituting the single-stranded moiety is not especially limited, and is preferably a sequence not forming a high order structure through intramolecular folding such as self-annealing, a sequence not impairing the base pair formation of the double-stranded moiety, or a sequence not base paired with the first or second target nucleic acid complementary region.

The hairpin region is formed by linking either combination of the 5'-end and 3'-end present at both ends of the double-stranded moiety to the 3'-end and the 5'-end of the single-stranded moiety via phosphodiester bonds.

In the clamping probe of the present invention, the hairpin region links the first target nucleic acid complementary region and the second target nucleic acid complementary region to each other as described above. There are two patterns of this linking. In one pattern, the hairpin region links, via the phosphodiester bond, the 3'-end of the first target nucleic acid complementary region and the 5'-end of the second target nucleic acid complementary region to each other, and in the other pattern, the hairpin region links, via the phosphodiester bond, the 3'-end of the second target nucleic acid complementary region and the 5'-end of the first target nucleic acid complementary region to each other. Either of these linking patterns may be employed.

(5) Double-Stranded Region

The "double-stranded region" (0105 or 0305) is a region linked to an end of each of the first and second target nucleic acid complementary regions not linked to the hairpin region. The basic structure of the double-stranded region is equivalent to that of the double-stranded moiety of the hairpin region. In other words, it consists of double strands having mutually complementary nucleotide sequences each of 3 to 10 bases, preferably 4 to 9 bases, 4 to 8 bases, 5 to 7 bases, or 5 or 6 bases. Besides, the nucleotide sequences constituting the double-stranded region are not especially limited, and are preferably nucleotide sequences having a large GC content. There is no need, however, that it has the same base length and/or the same nucleotide sequence as the double-stranded moiety of the hairpin region.

As described above, in the clamping probe of the present invention, the hairpin region links the first target nucleic acid complementary region and the second target nucleic acid complementary region by either of the two patterns. No matter which pattern is employed by the hairpin region for the linking, each of the first target nucleic acid complementary region and the second target nucleic acid complementary region still has another combination of the 5'-end and the 3'-end as free ends. The double-stranded region is linked to these ends via phosphodiester bonds.

(3) Spacer Region

The "spacer region" (0106) is a selective component in the clamping probe of the present invention, and is a region placed between the first and/or the second target nucleic acid complementary region and the hairpin region, and/or between the first and/or the second target nucleic acid complementary region and the double-stranded region. It may be placed in all the spaces between these four regions, or may be placed in any one, two or three of the spaces between the regions. When the spacer region is placed, the degree of freedom of the first target nucleic acid complementary region and/or the second target nucleic acid complementary region in the clamping probe is improved, and hence the first and/or the second target nucleic acid complementary region can be easily bound to the corresponding target nucleic acid region.

The spacer region consists of a nucleotide sequence of 1 to 5 bases, and preferably 1 to 4 bases or 1 to 3 bases. The nucleotide sequence of the spacer sequence is not especially limited as long as it is a sequence not forming a high order structure through intramolecular folding such as self-annealing.

(7) G-Quartet Region

The "G-quartet region" (0107) is a selective component in the clamping probe of the present invention, and is a region linked to at least one of the 5'-end (corresponding to the free 5'-end of the double-stranded region) and the 3'-end (corresponding to the free 3'-end of the double-stranded region) of the clamping probe.

Figure 2:
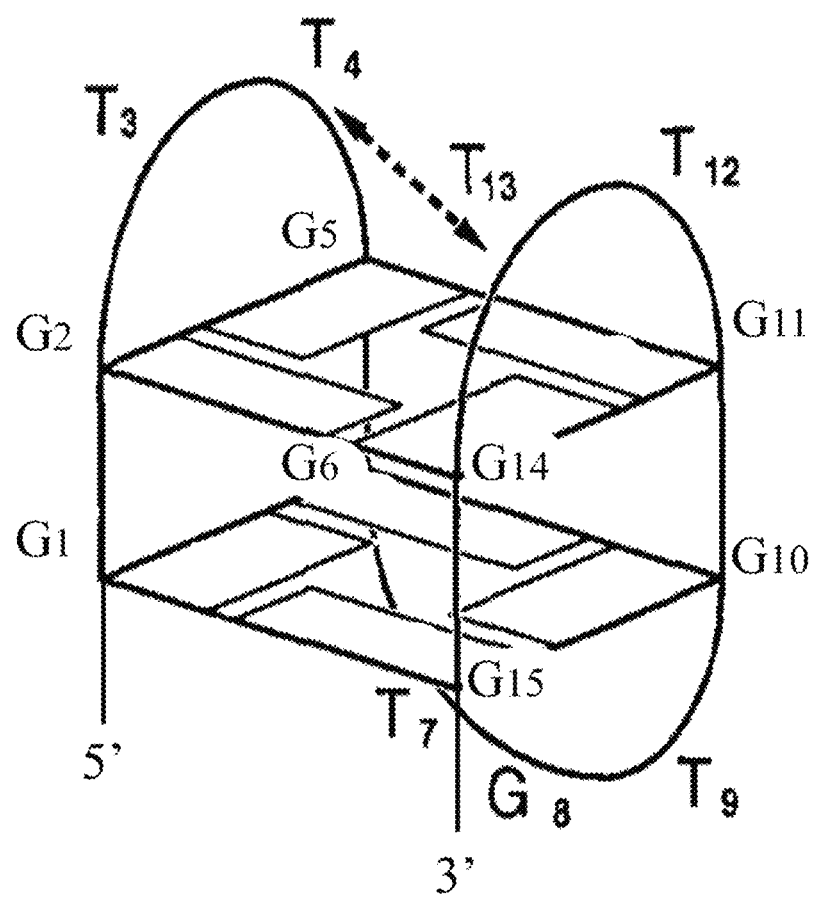
FIG. 2 shows a G-quartet structure constituting a G-quartet region that may be connected to a free end of the clamping probe of the present invention. This structure has a characteristic that four Gs (for example, G2, G5, G11 and G14 or G1, G6, G10 and G13 in this figure) are placed on the same plane via hydrogen bonds, and such a plane is formed two or more.

The G-quartet consists of a single-stranded nucleic acid molecule forming a quadruplex structure (quadruplex spiral structure) as shown in FIG. 2, in which four Gs in the nucleotide sequence of the nucleic acid molecule are placed on the same plane via hydrogen bonds, and such a plane is formed two or more. The G-quartet can be formed, via the intramolecular folding, in a single strand containing a G-rich nucleotide sequence such as 5'-GGTTGGTGTGGTTTGG-3' represented by SEQ ID NO: 3.

When the G-quartet region is linked to the clamping probe, amplification of a non-target allele in a target gene can be strongly inhibited in a nucleic acid amplification reaction performed in a mutant gene detection method described later.

(8) Flanking Region

The "flanking region" (0108) is a selective component in the clamping probe of the present invention, and is a single-stranded nucleic acid region linked to the 5'-end and/or the 3'-end of the clamping probe. Accordingly, the flanking region is a single-stranded nucleic acid region linked to the free 5'-end of the double-stranded region and/or the free 3'-end of the double-stranded region.

The base length of the flanking region is not especially limited. It is, however, preferably a length of 1 to 30 bases or 1 to 25 bases in general because an unnecessarily long length not only increases the cost necessary for the preparation of the clamping probe of the present invention but also causes a technical difficulty.

A nucleic acid constituting the flanking region may be any of the aforementioned nucleic acids. It is preferably a naturally occurring nucleic acid, and more preferably a DNA. Besides, the nucleotide sequence of the flanking region may be any sequence not base paired with another region (including another flanking region) of the clamping probe. It may be a sequence forming a high order structure via the intramolecular folding such as self-annealing. In this point, the G-quartet region can be regarded as one form of the flanking region. It is noted that the flanking region may be further linked to the free end of the G-quartet region.

(9) Clamping Probe

The entire structure of the clamping probe (0100) of the present invention is described below.

The basic structure of the clamping probe of the present invention is a structure in which one end of the first target nucleic acid complementary region (0101) and one end of the second target nucleic acid complementary region (0102) are linked to each other via the hairpin region (0104), and the other ends thereof are linked to the double-stranded region (0105) (FIG. 1). Besides, if necessary, the spacer region (0106) can be inserted between any of the aforementioned regions, or the G-quartet region (0107) or the flanking region (0108) can be linked to the 5'-end and/or the 3'-end of the clamping probe.

The clamping probe is constituted by a naturally occurring nucleic acid. If necessary, however, it may partially contain a non-naturally occurring nucleic acid and/or a nucleic acid analog. For example, the spacer region may be replaced with a nucleic acid analog. Besides, the naturally occurring nucleic acid may be any of a DNA, an RNA and a combination of these, and is preferably a DNA in the light of the cost required for the synthesis and stability against a nuclease.

The clamping prove may be fixed on a support at the 5'-end or the 3'-end. Examples of the "support" used herein include a low molecular weight compound (such as biotin, avidin, streptavidin or neutravidin), an amino acid or a peptide, a polymer polysaccharide support (such as sepharose, sephadex or agarose), a resin (a natural resin or a synthetic resin including a plastic), silica, glass, a magnetic bead, a metal (such as gold, platinum or silver), a ceramic, or a combination of any of these. If the flanking region is linked to the 5'-end and/or the 3'-end of the clamping probe, a free end portion of the flanking region may be fixed on the support because the free end portion of the flanking region corresponds to the end of the clamping probe.

The clamping probe of the present invention specifically recognizes and firmly binds to the target nucleic acid molecule through the complementary strands contained in the molecule. The mismatch site of the first target nucleic acid complementary region of the clamping probe of the present invention is, however, not complementary to the corresponding base of the wild-type target nucleic acid molecule. Besides, at the same time, the mutation complementary site is complementary to the base of the known mutation site of the wild-type target nucleic acid molecule but is not complementary to the base of the known mutation site of the mutant-type target nucleic acid molecule. Owing to this difference in the complementarity of the clamping probe to the wild-type target nucleic acid molecule and the mutant-type target nucleic acid molecule, a difference is caused in the binding stability.

Besides, a complementary region to the target nucleic acid molecule is present in two positions of the first target nucleic acid complementary region and the second target nucleic acid complementary region to be separated from each other via the hairpin region in the molecule. Therefore, the clamping probe has bispecificity so that a case of binding of merely one of the complementary regions and a case of binding of both the complementary regions can be distinguished.

The clamping probe of the present invention can be used as a PCR clamping probe or a molecular sieve clamping probe by utilizing the aforementioned characteristics. A specific method for using the clamping probe is described in detail as a second aspect.

1-4. Production of Clamping Probe

A production method for the clamping probe of the present invention is described herein. The production method for the clamping probe of the present invention is not especially limited as long as a single-stranded nucleic acid molecule having the aforementioned structure can be prepared. The clamping probe can be produced by any of methods known in this art. It can be produced by referring to, for example, a method described by Green, M. R. and Sambrook, J., 2012, Molecular Cloning: A Laboratory Manual Fourth Ed., Cold Spring Harbor Laboratory Press, Cold Spring Harbor, N.Y. The production method is herein specifically described with reference to specific examples, but the method is not limited to that described below.

The production method for the clamping probe of the present invention comprises (1) a design step, (2) a synthesis step and (3) an intramolecular folding step. The respective steps are specifically described below.

(1) Design Step

The "design step" refers to a step of determining the structure of the clamping probe of the present invention and the nucleotide sequence constituting it.

In this step, a target nucleic acid molecule is first determined. Candidates of nucleic acid molecules are not limited, and are suitably genes having known mutation or transcripts thereof. In particular, a gene that causes a malignant neoplasm (a malignant tumor, what is called a cancer) due to postnatal occurrence of known mutation in a genome DNA within a specific cell is a suitable target nucleic acid molecule for the clamping probe of the present invention. Examples include KRas gene that causes colorectal cancer or pancreatic cancer, EGFR gene that causes non-small cell lung cancer (NSCLC) and RET gene that causes thyroid medullary carcinoma when known mutation occurs.

Next, a first target nucleic acid region is determined. As the first target nucleic acid region, continuous 15 to 30 bases, preferably 15 to 20 bases of a wild-type target nucleic acid molecule (wild-type gene) are selected so that the resultant Tm value can be 40° C. to 70° C., preferably 50° C. to 65° C. At this point, it is designed to contain a known mutation site within the region. The known mutation site is preferably designed to be placed within at least 3 bases, 4 bases, 5 bases, 6 bases, 7 bases or 8 bases from both ends of the first target nucleic acid region. The first target nucleic acid region may be designed to contain a known mutation site of 2 or more bases.

Subsequently, a second target nucleic acid region is determined. As the second target nucleic acid region, continuous 15 to 30 bases, preferably 15 to 20 bases adjacent to the first target nucleic acid region in the target nucleic acid molecule are selected. It may be on either the 5'-end side or the 3'-end side of the first target nucleic acid region, and the Tm value of the second target nucleic acid region is preferably set to 40° C. to 70° C., preferably 50° C. to 65° C. In the target nucleic acid molecule, the first target nucleic acid region and the second target nucleic acid region may be designed to be adjacent to each other, or can be designed to be spaced from each other by 1 to 5 bases, preferably 1 to 3 bases.

The nucleotide sequences of a first target nucleic acid complementary region and a second target nucleic acid complementary region of the clamping probe consist of nucleotide sequences complementary respectively to the nucleotide sequences of the first target nucleic acid region of the wild-type target nucleic acid molecule and the second target nucleic acid region of the target nucleic acid molecule in principle. Accordingly, these complementary regions are simultaneously determined by determining the target nucleic acid regions. The first target nucleic acid complementary region can be, however, if necessary, designed to contain a mismatch site not complementary to the first target nucleic acid region of the wild-type target nucleic acid molecule. The mismatch site may be any of bases contained in the first target nucleic acid complementary region excluding a mutation complementary site. Besides, the number of bases of the mismatch site may be 1 to 3 bases, 1 to 2 bases or 1 base. If plural mismatch sites are contained, the respective mismatch sites may be continuous to or spaced from one another in the first target nucleic acid complementary region.

Next, a hairpin region of the clamping probe is designed. The hairpin region is designed so that a single-stranded molecule, which is formed by linking, through a single-stranded moiety of 3 to 10 bases, the 3'-end of one nucleic acid strand of a double-stranded moiety consisting of mutually complementary nucleotide sequences each of 4 to 9 bases with the 5'-end of the other nucleic acid strand, can form a stem and loop structure by the intramolecular folding. The nucleotide sequence constituting the double-stranded moiety is not limited, and is designed so that the single-stranded moiety may have a large GC content. Besides, a nucleic acid constituting the double-stranded nucleic acid portion is preferably a DNA, and may additionally contain an artificial nucleic acid if necessary. The nucleotide sequence constituting the single-stranded moiety is also not limited, and a nucleotide sequence not forming a high order structure within the single-stranded moiety via the self-annealing or the like, a nucleotide sequence not impairing base pair formation of the double-stranded moiety, or a nucleotide sequence not base paired with the first or the second target nucleic acid complementary region is preferably designed.

When the nucleotide sequence of the hairpin region is determined, the three regions of the first target nucleic acid region, the second target nucleic acid region and the hairpin region are designed to be connected to one another. At this point, there are two linking patterns, as shown in FIG. 4 and described below, between the clamping probe and the target nucleic acid molecule depending on the linking position of the hairpin region.

Figure 4A:
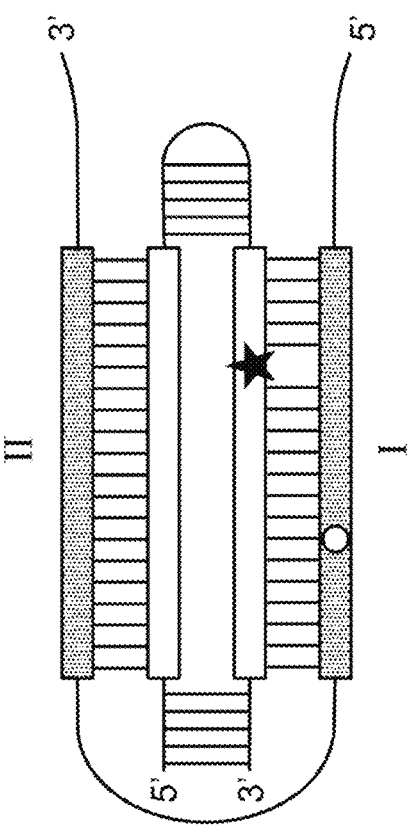
FIGS. 4A to 4D are diagrams showing two types of binding relationships between the clamping probe of the present invention and a target nucleic acid molecule.
Figure 4B:
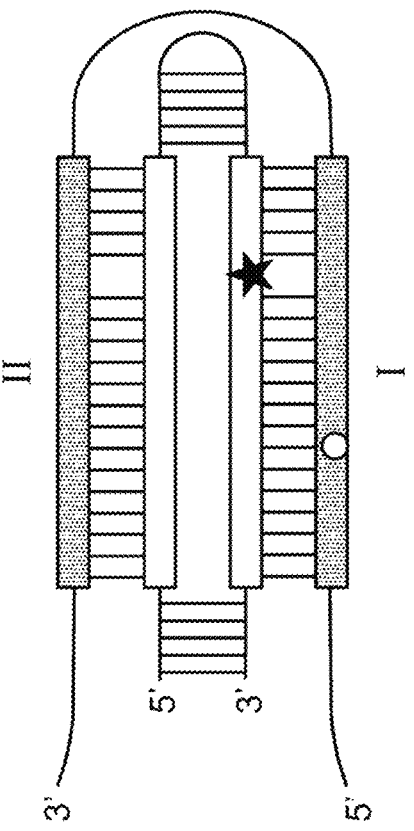

(i) Diamond-Type (FIGS. 4A and 4B)

If the second target nucleic acid region (II) of the target nucleic acid molecule is placed on the 5'-end side of the first target nucleic acid region (I), there is a linking pattern in which the 3'-end of the first target nucleic acid complementary region and the 5'-end of the second target nucleic acid complementary region of the clamping probe are linked to each other (FIG. 4A). Furthermore, if the second target nucleic acid region (II) of the target nucleic acid molecule is placed on the 3'-end side of the first target nucleic acid region (I), there is a linking pattern in which the 3'-end of the second target nucleic acid complementary region and the 5'-end of the first target nucleic acid complementary region of the clamping probe are linked to each other (FIG. 4B).

In this linking pattern, the clamping probe and the target nucleic acid molecule are connected with their ends placed in the opposite directions.

Figure 4C:
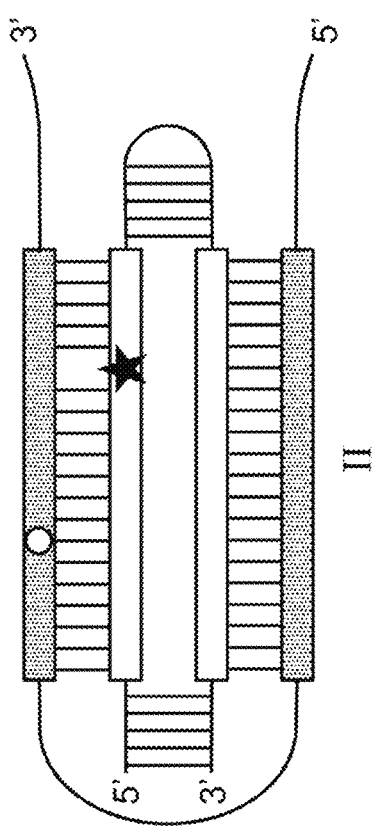
Figure 4D:
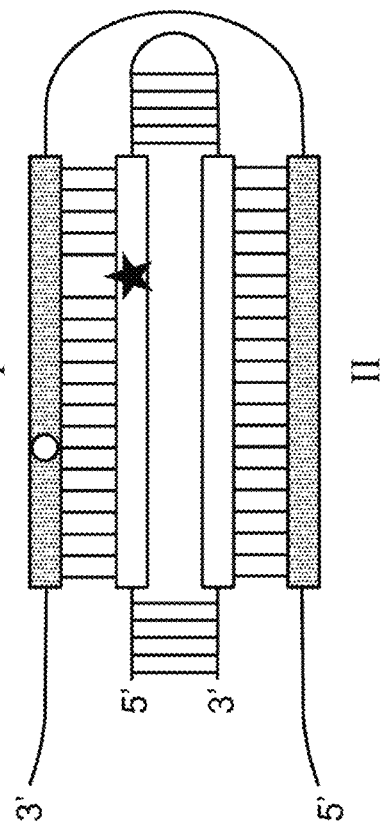

(ii) Parallel-Type (FIGS. 4C and 4D)

If the second target nucleic acid region (II) of the target nucleic acid molecule is placed on the 5'-end side of the first target nucleic acid region (I), there is a kinking pattern in which the 3'-end of the first target nucleic acid complementary region and the 5'-end of the second target nucleic acid complementary region of the clamping probe are linked to each other (FIG. 4C). If the second target nucleic acid region (II) of the target nucleic acid molecule is placed on the 3'-end side of the first target nucleic acid region (I), there is a linking pattern in which the 3'-end of the second target nucleic acid complementary region and the 5'-end of the first target nucleic acid complementary region of the clamping probe are linked to each other (FIG. 4D).

In this linking pattern, the clamping probe and the target nucleic acid molecule are connected with their ends placed in the same direction.

Either of the diamond-type linking or the parallel-type linking may be employed for the design. The parallel-type connection is preferred.

Finally, a double-stranded region is designed. The double-stranded region can be designed in the same manner as the double-stranded moiety. If necessary, a spacer region of 1 to 5 bases can be designed to be placed between any two of the regions, or a G-quartet region and/or a flanking region can be designed to be placed at the free end of the double-stranded region.

(2) Synthesis Step

The "synthesis step" refers to a step of performing synthesis based on nucleotide sequence information of the clamping probe designed in the design step. A clamping probe is a nucleic acid molecule having a total length of 50 to 200 bases, and consists of a naturally occurring nucleic acid in principle. Accordingly, the clamping probe of the present invention can be chemically synthesized by a synthesis method known in this art. For example, chemical synthesis by a solid-phase synthesis method can be employed. Specifically, a chemical synthesis method described in, for example, Current Protocols in Nucleic Acid Chemistry, Volume 1, Section 3, Verma S. and Eckstein F., 1998, Annul Rev. Biochem., 67, 99-134 can be employed. Besides, with regard to chemical synthesis of nucleic acids including artificial nucleic acids and modified nucleic acids, a large number of life science manufacturers (such as Takara Bio Inc., Fasmac Co., Ltd., Life Technologies Corporation, Gene Design, Inc. and Sigma Aldrich) provide a contracted manufacturing service, and such a service can be utilized. The clamping probe chemically synthesized is preferably purified before use by a method known in this art. Examples of the purification method include a gel purification method, an affinity column purification method and an HPLC method.

(3) Intramolecular Folding Step

The "intramolecular folding step" refers to a step of forming the clamping probe of the present invention by the intramolecular folding of the clamping probe after the synthesis step.

In this step, the production can be performed by placing the synthesized clamping probe of the single-stranded nucleic acid molecule in a condition capable of intramolecular folding. For example, the synthesized clamping probe may be dissolved in and mixed with an appropriate buffer such as PBS(-) (0.2 g/L KCl, 8 g/L NaCl, 0.2 g/L $KH_2PO_4$, and 1.15 g/L $Na_2HPO_4$), the resultant is heated to 90° C. and then the temperature is gradually lowered so as to cause the intramolecular folding.

2. Method for Detecting Presence of Known Mutation in Target Nucleic Acid Molecule 2-1. Outline The second aspect of the present invention is a method for detecting presence of known mutation in a target nucleic acid molecule (herein frequently referred to as the "mutation detection method"). According to the method of the present invention, it can be sensitively detected whether or not a mutant nucleic acid molecule of interest is contained in a nucleic acid sample containing a target nucleic acid molecule.

2-2. Method

The mutation detection method of the present invention comprises a clamping probe binding step and a mutation detecting step. These steps are now specifically described.

(1) Clamping Probe Binding Step

The "clamping probe binding step" is a step of binding the clamping probe to a target nucleic acid molecule by mixing the clamping probe described in the first aspect with a nucleic acid sample containing a target nucleic acid molecule.

The "nucleic acid sample" refers to a sample used in the mutation detection method of the present invention, and is mainly constituted by a nucleic acid. Examples include a DNA (including a genome DNA and a cDNA) and an RNA (including an mRNA and a non-coding RNA). It may contain a single type of nucleic acid, and alternatively, may be a nucleic acid pool containing plural types of nucleic acids such as a genome DNA and an mRNA derived from a cell or a tissue.

The clamping probe used in this step is a clamping probe for a target nucleic acid molecule for detecting presence of known mutation. The first target nucleic acid complementary region of the clamping probe excluding the mismatch site is complementary to the wild-type target nucleic acid molecule in principle, but cannot be complementary to the mutant-type target nucleic acid molecule even in the mutation complementary site.

The mixing of the nucleic acid sample and the clamping probe is not especially limited as long as it is performed under a condition where the target nucleic acid molecule and the clamping probe can be annealed. For example, the nucleic acid sample and the clamping probe may be mixed in an appropriate buffer such as PBS(-) (0.2 g/L KCl, 8 g/L NaCl, 0.2 g/L $KH_2PO_4$, and 1.15 g/L $Na_2HPO_4$).

(2) Mutation Detecting Step

The "mutation detecting step" is a step of detecting mutation of the target nucleic acid molecule based on a difference in binding force between the target nucleic acid molecule and the clamping probe caused depending on the presence of the mutation in the target nucleic acid molecule.

As described in the first aspect, the clamping probe of the present invention is different in the complementarity in the mutation complementary site between the wild-type target nucleic acid molecule and the mutant-type target nucleic acid molecule. Besides, since there are two complementary regions to the target nucleic acid molecule, it has bispecificity so that a case of binding of merely one of the complementary regions and a case of binding of both the complementary regions can be distinguished.

The term "based on a difference in binding force" refers to use of a difference in the binding stability caused depending on whether the clamping probe binds to the wild-type target nucleic acid molecule or the mutant-type target nucleic acid molecule. Based on the difference in the binding force, the clamping probe of the present invention can be used for detecting the presence of the mutant-type target nucleic acid molecule, for example, as a nucleic acid amplification probe by employing the nucleic acid amplification method, or as a molecular sieve clamping probe by employing the molecular sieve.

(i) Detection by Nucleic Acid Amplification Method

The detection by the nucleic acid amplification method is a method for detecting the difference in the binding force of the clamping probe caused between the wild-type target nucleic acid molecule and the mutant-type target nucleic acid molecule as an amount difference of an amplified product. If the clamping probe is used as the nucleic acid amplification clamping probe, amplification of the target nucleic acid molecule having a base complementary to the base of the mutation complementary site is inhibited due to rigid binding of the clamping probe of the present invention. On the other hand, amplification of the target nucleic acid molecule not complementary to the base of the mutation complementary site is not inhibited because the binding of the clamping probe is weakened at a temperature at which denaturation occurs in the nucleic acid amplification reaction. Accordingly, in order to detect the presence of the mutant-type target nucleic acid molecule present mixedly with the wild-type target nucleic acid molecule, the clamping probe containing the first target nucleic acid complementary region complementary to the first target nucleic acid region of the wild-type target nucleic acid molecule can be used. In this manner, the amplification of the wild-type target nucleic acid molecule is inhibited and the mutant-type target nucleic acid molecule is selectively amplified, and hence, the mutant-type target nucleic acid molecule can be detected.

Herein, the "nucleic acid amplification method" refers to a method for specifically amplifying a detection region in a nucleic acid molecule by using an amplification primer. The nucleic acid amplification reaction used in the present embodiment can employ any nucleic acid amplification method as long as a detection region can be amplified. Examples include the PCR method, the ICAN method and the LAMP method.

The "detection region" is a region in the target nucleic acid molecule to be amplified by an amplification primer. In this step, a region in the target nucleic acid molecule including the first target nucleic acid region and the second target nucleic acid region is amplified as the detection region.

The "amplification primer" is a primer used for amplifying the detection region by the nucleic acid amplification method. The amplification primer is constituted by a naturally occurring nucleic acid such as a DNA or an RNA, or an LNA, or a combination of these. In the nucleic acid amplification method, the amplification primer is used as a pair of a forward primer and a reverse primer. The number of bases of each amplification primer is not especially limited as long as it is 10 to 40 bases. The number of bases is preferably 15 to 30 bases. Besides, the sequence of the amplification primer is not limited as long as the Tm value is 50 to 65° C. A distance between the amplification primers, namely, the detection region, is not limited as long as it is 100 to 400 nucleotides or 100 to 300 nucleotides.

The nucleic acid amplification method can be specifically performed with reference to a method described by Green, M. R. and Sambrook, J., 2012 (vide supra) or the like.

In this step, it is preferable to use, as a negative control, a nucleic acid sample containing a target nucleic acid molecule having been revealed to have no known mutation in a mutation site at least within an amplification region, preferably containing merely a wild-type target nucleic acid molecule, so as to obtain a detection result by the nucleic acid amplification method performed under the same conditions.

The amplified product, that is, the detection region amplified by the nucleic acid amplification method, can be detected by a nucleic acid determination method known in this art. For example, the amplified product can be subjected to gel electrophoresis, and then stained with an intercalator such as ethidium bromide for comparison to find the amount difference from the amplified product of the negative control. In order to quantitatively determine the amount of the amplified product, the nucleic acid amplification method can be performed by a quantitative nucleic acid amplification method, such as a real-time PCR method, in which the increase of the amplified product is detected over time as the increase of fluorescence intensity or the like. Examples of the real-time PCR method include a TaqMan® probe method, a cycling probe method, and a method in which a nucleic acid staining agent such as SYBER Green I is added to a gene amplification reaction solution to perform staining together with a gene amplification reaction, so as to measure, under irradiation with excitation light, the increase of an amplified product as intensity of fluorescence emitted from the intercalated nucleic acid staining agent, and any of these methods can be employed. These nucleic acid amplification methods are all known techniques, and can be performed by a method described by Green, M. R. and Sambrook, J., 2012 (vide supra) and the like. Besides, a kit utilizing the quantitative nucleic acid amplification method is commercially available from various manufacturers, and such a kit may be used. An example includes SYBR Premix Extaq (Takara Bio Inc.). For the detection and the quantitative determination of the amplified product, a real-time PCR thermal cycler system device commercially available from various manufacturers may be used.

(ii) Detection by Molecular Sieve

The detection by the molecular sieve is a method for detecting the difference in the binding force of the clamping probe caused between the wild-type target nucleic acid molecule and the mutant-type target nucleic acid molecule by sieving depending on the size of the nucleic acid molecule. If the clamping probe is used as the molecular sieve clamping probe, the target nucleic acid molecule having a base complementary to the base of the mutation complementary site is increased in the molecular size due to the rigid binding of the clamping probe of the present invention, and hence is easily trapped by the molecular sieve. Therefore, the mobility of the wild-type target nucleic acid molecule via the molecular sieve is suppressed more largely than the mobility of the mutant-type target nucleic acid molecule, and hence, the mutant-type target nucleic acid molecule can be detected based on the size difference. The molecular sieve is not limited, but a molecular sieve of gel electrophoresis using an agarose gel or a polyacrylamide gel is generally used, and can be used in this step. The type and the concentration of gel may be appropriately selected in accordance with the molecular weight size of the amplified product. In this step, a 10 to 15% polyacrylamide gel is suitably used, but this is not restrictive. After developing the nucleic acid molecule by the electrophoresis, the amplified product of interest may be detected by staining with an intercalator such as ethidium bromide, detected by a southern hybridization method using an appropriate probe, detected by a chromatographic hybridization method using a gold nanoparticle, or detected by measuring turbidity of a solution caused by the amplified gene.

3. Method for Determining Whether a Subject is Affected with Genetic Disease

3-1. Outline

A third aspect of the present invention is a method for determining whether a subject is affected with a genetic disease. The present invention provides a method applying the mutation detection method of the second aspect, and if an in vitro sample collected from the subject is used for detecting the presence of known mutation in a target gene contained in the sample, and determining whether a subject is affected with a genetic disease can be aided.

Incidentally, the method of this aspect is a method for aiding diagnosis by a doctor, namely, final determination of whether or not a subject is affected with a genetic disease by determining that the subject is liable to be affected with the genetic disease. Accordingly, the term "method for determining whether a subject is affected with a genetic disease" herein is not included in medical practice.

Herein, the term "genetic disease" refers to a disease caused by mutation of a gene. It may be either a congenital genetic disease or an acquired genetic disease caused by mutation, and is preferably an acquired genetic disease. Examples include tumors (including cancers).

The genetic disease corresponding to a target of the present invention is not especially limited as long as a target gene causing the disease and its mutation site are known. Examples include colorectal cancer whose target gene is the KRas gene and non-small cell lung cancer whose target gene is the EGFR gene. Besides, the mutation sites can be g34a, g34c, g35a, g35c, g35t and g38a in the KRas gene, and g2115t, g2155a, t2573g, t2582a, g2235$\Delta$c2249(15), g2236$\Delta$a2250(15), t2240$\Delta$a2251(12), t2240$\Delta$c2257(16), t2239$\Delta$a2247(9) and a2238$\Delta$c2255(18) in the EGFR gene.

3-2. Method

The method of the present invention comprises a nucleic acid sample preparation step, a detection step and a determination step. The respective steps are described below.

(1) Nucleic Acid Sample Preparation Step

The "nucleic acid sample preparation step" is a step of preparing a nucleic acid sample from a biological sample obtained from a subject.

Herein, the term "subject" refers to an individual providing a biological sample to be used in the method of the present invention. A preferable subject is an individual liable to be affected with a genetic disease, and can comprise an individual whose possibility of being affected with a genetic disease is unknown, such as an examinee of a physical examination. Incidentally, the term "healthy individual" herein refers to a healthy individual that is healthy with respect to at least a genetic disease to be determined. Accordingly, an individual affected with a disease different from the disease to be determined is included in the healthy individual, but it is preferably a healthy individual in a narrow sense not affected with any disease, namely, an individual in good health.

Herein, the term "biological sample" refers to one collected from the subject to be used in the method of the present invention, and corresponds, for example, to a tissue, a cell, a body fluid or a peritoneal lavage fluid. The "tissue" or "cell" herein may be derived from any region of the subject, and is preferably a tissue or a cell collected in a biopsy or surgically cut. The tissue or the cell can be collected by obtaining one collected in a biopsy or surgically cut. Besides, the "body fluid" refers to a fluid sample collected from the subject. Examples include blood (including serum, plasma and an interstitial fluid), a spinal fluid (a cerebrospinal fluid), urine, lymph, digestive juices, ascites fluid, pleural fluid, fluid surrounding nerve roots, and extracts of respective tissues and cells. It is preferably blood or a spinal fluid. The body fluid may be collected by a method known in this art. For example, a spinal fluid can be collected by known lumbar puncture or collected from a surgical field at the time of an operation, and blood or lymph may be collected by a known blood sampling method.

The biological sample may be used immediately in the method of the present invention after the collection, or may be frozen or refrigerated for a prescribed period of time and thereafter subjected to a thawing or heating treatment if necessary before use.

As a method for preparing the nucleic acid sample from the biological sample, any known technique for preparing a nucleic acid from a cell or the like may be employed. For example, a nucleic acid preparation method described by Green, M. R. and Sambrook, J., 2012 (vide supra) or the like can be referred to, and since various nucleic acid preparation kits are commercially available from various life science product manufactures, any of these can be used.

(2) Detection Step

The "detection step" is a step of detecting the presence of known mutation in the target gene by using the nucleic acid sample obtained in the nucleic acid sample preparation step. This step may be performed in the same manner as in the mutation detecting step of the second aspect. A detection result is preferably quantified.

(3) Determination Step

The "determination step" is a step of determining that the subject is likely to be affected with the genetic disease involving the target gene if the target gene having the mutation is detected in the nucleic acid sample as a result of the detection step.

As a specific determination method, for example, a measurement value obtained from the subject by quantifying a result of the detection step (measurement value of a subject) is compared with a measurement value obtained from a healthy individual by quantifying a result of the detection step (measurement value of a healthy individual), and if there is a statistically significant difference between these measurement values, it is determined that the subject is liable to be affected with the genetic disease involving the target gene.

Herein, the term "statistically significant" comprises a case where a significance level (a level of significance) between the measurement values of the subject and the healthy individual having been statistically processed is lower than 5%, 1%, 0.3%, 0.2% or 0.1%. A test method for the statistic processing is not especially limited, and any known test method capable of determining significance may be appropriately employed. For example, Student's t-test method or a multiple comparison test method can be employed.

EXAMPLES

Example 1: Preparation of Clamping Probe (Purpose)

A clamping probe according to the present invention using the KRas gene as a target nucleic acid molecule was prepared.

(Method)

On the basis of the nucleotide sequence represented by SEQ ID NO: 1, positions 23 to 42 and positions 1 to 20 were selected respectively as the first target nucleic acid region and the second target nucleic acid region. Besides, as the known mutation in the first target nucleic acid region of mutant-type KRas gene, g34t homo causing G12C mutation in KRAS was selected. A first target nucleic acid complementary region and a second target nucleic acid complementary region of the clamping probe were set to have nucleotide sequences respectively complementary to these target nucleic acid regions. As a hairpin region, 5'-ggagggaacctcc-3' represented by SEQ ID NO: 4 was used. In this sequence, positions 1 to 5 and positions 9 to 13 correspond to a double-stranded moiety, and positions 6 to 8 corresponds to a single-stranded moiety. The 5'-end and the 3'-end of the hairpin region are designed to be respectively connected to the 3'-end of the first target nucleic acid complementary region and the 5'-end of the second target nucleic acid complementary region. Double-stranded regions were designed to be positions 1 to 5 and positions 9 to 13 of the nucleotide sequence represented by SEQ ID NO: 4 in the same manner as the double-stranded moiety of the hairpin region, and were designed to be connected respectively to the 5'-end of the first target nucleic acid complementary region and the 3'-end of the second target nucleic acid complementary region. A nucleotide sequence of a full match-type clamping probe completely complementary to the wild-type KRas gene is set forth in SEQ ID NO: 5, a nucleotide sequence of a mutant-type KRas gene a27c clamping probe is set forth in SEQ ID NO: 6, a nucleotide sequence of a mutant-type KRas gene a33c clamping probe is set forth in SEQ ID NO: 7, a nucleotide sequence of a mutant-type KRas gene a36t clamping probe is set forth in SEQ ID NO: 8, a nucleotide sequence of a mutant-type KRas gene c37g clamping probe is set forth in SEQ ID NO: 9, and a nucleotide sequence of a mutant-type KRas gene g39c clamping probe is set forth in SEQ ID NO: 10.

On the basis of the designed sequence information, each clamping probe was prepared by chemical synthesis. Synthesis of DNA oligonucleotides as the clamping probes was entrusted to Fasmac Co., Ltd. None of nucleic acids were modified. Each synthesized clamping probe was dissolved in D-PBS(−) (0.2 g/L KCl, 8 g/L NaCl, 0.2 g/L $KH_2PO_4$, and 1.15 g/L $Na_2HPO_4$), the resultant was heated to 90° C., and then the temperature was gradually lowered for performing the intramolecular folding, and thus, the clamping probes of the present invention were prepared.

Example 2: Detection of Mutant-Type KRas Gene by Nucleic Acid Amplification Method (Purpose)

Each KRas gene clamping probe prepared in Example 1 was used for detecting mutant-type KRas gene by the nucleic acid amplification method.

(Method)

A genome DNA containing the KRas gene, that is, the target nucleic acid molecule, was extracted from HEK293 cell (human embryonic kidney cell) and MIAPaCa-2 cell that is a pancreatic cancer cell. The KRas gene derived from HEK293 cell is a wild-type KRas gene, and the MIAPaCa-2 cell is known to have homo of g34t mutant-type KRas gene expressing G12C (which means amino acid in position 12 mutated from glycine (G) to cysteine (C)) mutant-type KRAS. The extraction of the genome DNA was performed by using Mammalian Genomic DNA Miniprep Kit (Sigma-Aldrich) in accordance with accompanying protocol.

DNA amplification was performed by the PCR using each of the extracted genome DNAs as a template. For the DNA amplification by the PCR, 2 µL of 10× Paq Reaction buffer (Agilent Technologies), 1.6 µL of 2.5 mM dNTP, 0.2 µL of each of 10 µM KRas F & R primers (respectively set forth in SEQ ID NOS: 11 and 12), 1 ng of the genome DNA, 1 µL of 10 µM clamping probe, and 0.2 µL of 5 U/µL of Paq 5000 DNA polymerase (Agilent Technologies) were mixed with sterile water to prepare a PCR reaction solution in a total amount of 20 µL, and the amplification was performed under the following temperature conditions. After the PCR reaction solution was treated at 98° C. for 2 minutes to denature the DNA, the DNA amplification by the PCR was performed for 30 cycles each of 98° C. for 20 seconds, 55° C. for 20 seconds and 72° C. for 10 seconds. Thereafter, the resultant solution was allowed to stand still at 72° C. for 5 minutes, and then preserved at 10° C. The KRas F & R primers were prepared referring to primer sequences described by Huang Q., et al., Mol Cell Probes. 2010, 24: 376-380. Besides, as the clamping probes, in addition to the a27c clamping probe (FIG. 5A), an a33c clamping probe, an a36t clamping probe, a c37g clamping probe and a g39c clamping probe shown in FIG. 5B were used. As a negative control, a PCR reaction solution (None) containing no clamping probe was also prepared.

Each amplified product resulting from the PCR was developed by 12.5% non-denaturing polyacrylamide gel electrophoresis, and the resultant was stained with ethidium bromide.

(Results)

Figure 6A:
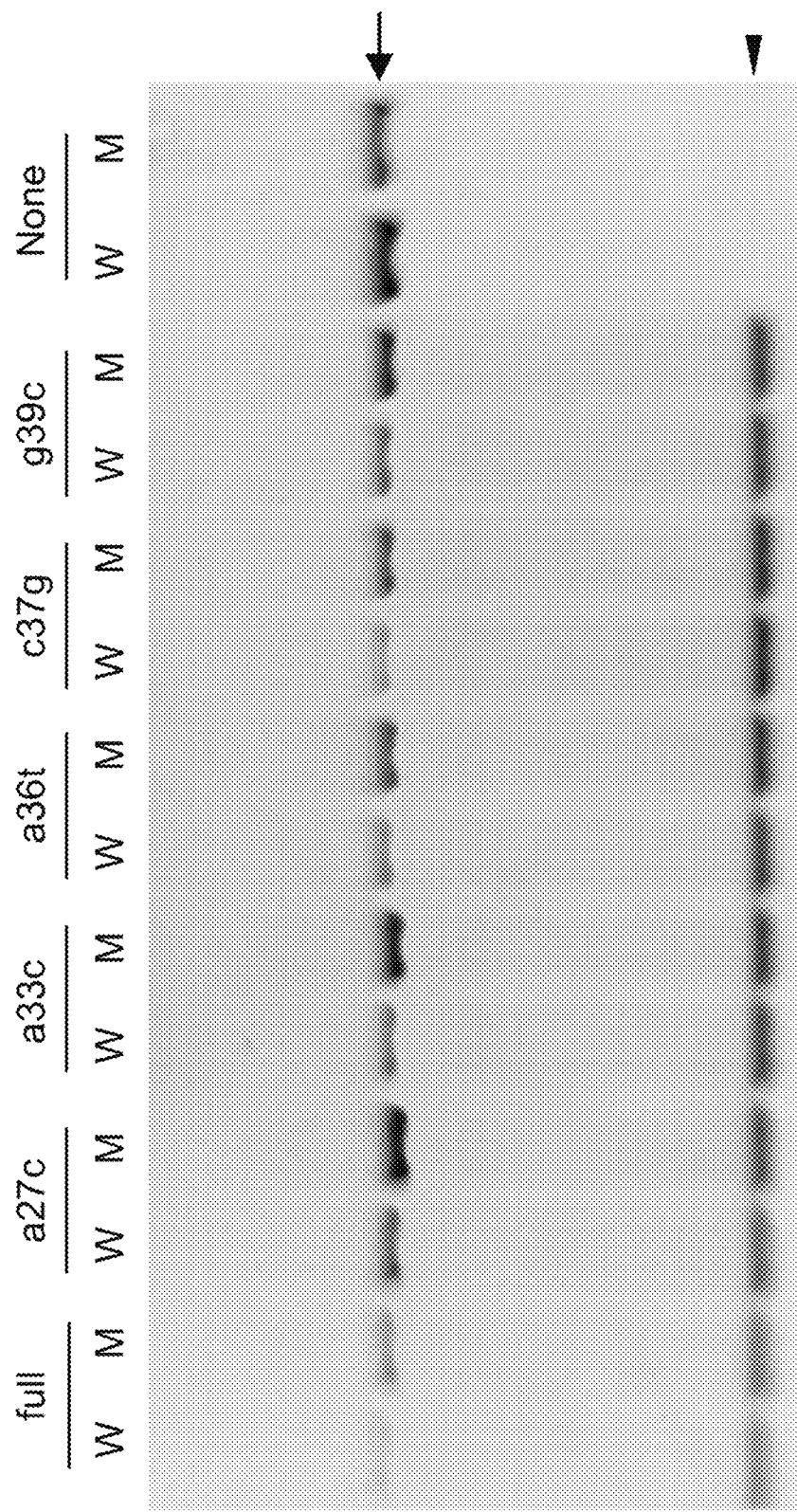
FIG. 6A shows a result of non-denaturing polyacrylamide gel electrophoresis of an amplified product obtained by nucleic acid amplification of mutant-type KRas gene using a KRas gene clamping probe. In this figure, "W" corresponds to a genome DNA containing wild-type KRas gene, and "M" corresponds to a genome DNA containing mutant-type KRas gene. A full match-type clamping probe and a mutant-type KRas gene clamping probe added are shown in an uppermost portion. In this figure, "full" corresponds to the full match-type clamping probe, "a27c", "a33c", "a36t", "c37g" and "g39c" correspond to mismatch-type clamping probes, an arrow points to amplified products in a detection region, and an arrowhead points to the clamping probes added.
Figure 6B:
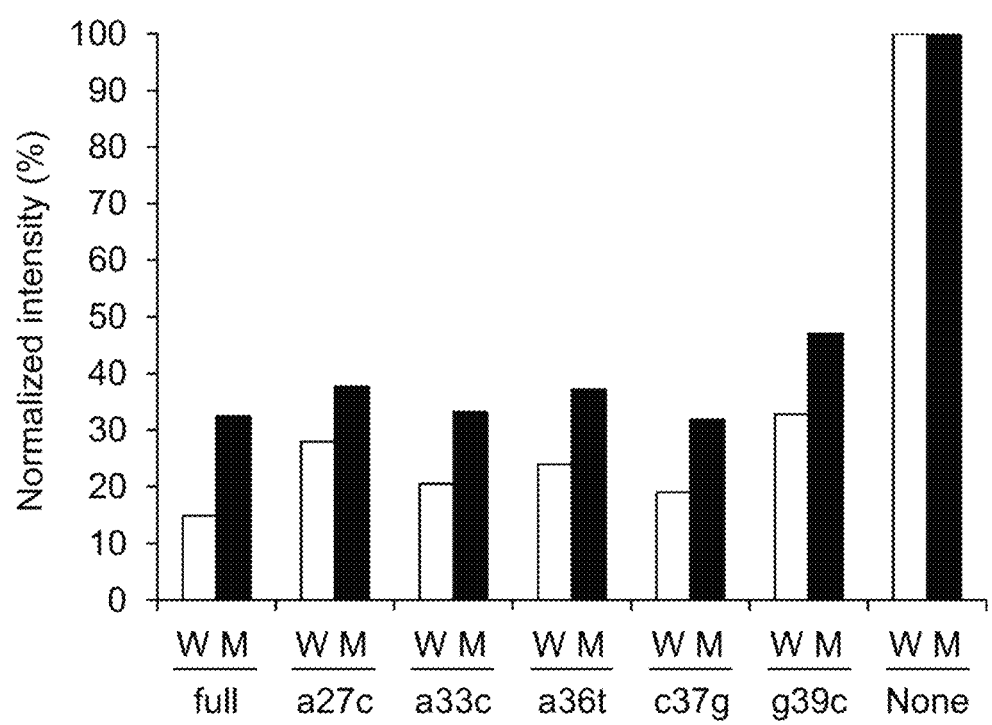
FIG. 6B is a diagram obtained by graphing out, using Image-J, bands pointed to by the arrow in FIG. 6B.

Results are shown in FIG. 6A and FIG. 6B. In each lane of FIG. 6A, "W" corresponds to the genome DNA derived from the HEK293 cell containing the wild-type KRas gene, and "M" corresponds to the genome DNA derived from the MIAPaCa-2 cell containing the mutant-type KRas gene.

It was revealed that the amplification of the detection region is inhibited in the genome DNA (W) containing the wild-type KRas gene as compared with that in the genome DNA (M) containing the mutant-type KRas gene no matter which of the mutant-type KRas gene clamping probes was added. On the other hand, in using the full match-type clamping probe in which the first target nucleic acid region is completely complementary to the wild-type KRas gene and merely the mutation site is not complementary to the mutant-type KRas gene, the amplification of the detection region is inhibited as compared with that in using the mismatch-type clamping probes, but it was revealed that the amplification of the wild-type KRas gene in the detection region is most strongly inhibited as shown in FIG. 6B.

Example 3: Detection of Mutant-Type KRas Gene by Molecular Sieve (Purpose)

It was verified whether or not mutant-type KRas gene can be detected at normal temperature not via the nucleic acid amplification reaction but via the molecular sieve using polyacrylamide gel.

(Method)

Oligonucleotides each consisting of 70 bases and respectively mimicking cDNAs of the wild-type KRas gene and the g34t mutant-type KRas gene were prepared by the chemical synthesis. These oligonucleotides were designated respectively as WT-70 (SEQ ID NO: 13) and MT-70(g34t) (SEQ ID NO: 14), and the synthesis was entrusted to Fasmac Co., Ltd. Ten (10) pmol of each of WT-70 and MT-70(g34t) was mixed with 10 pmol of full match-type clamping probe or g39c clamping probe in 8 µL, and the resultant was incubated at 37° C. for 1 hour. Each sample was developed by 12.5% non-denaturing polyacrylamide gel electrophoresis, and then stained with ethidium bromide.

(Results)

Figure 7:
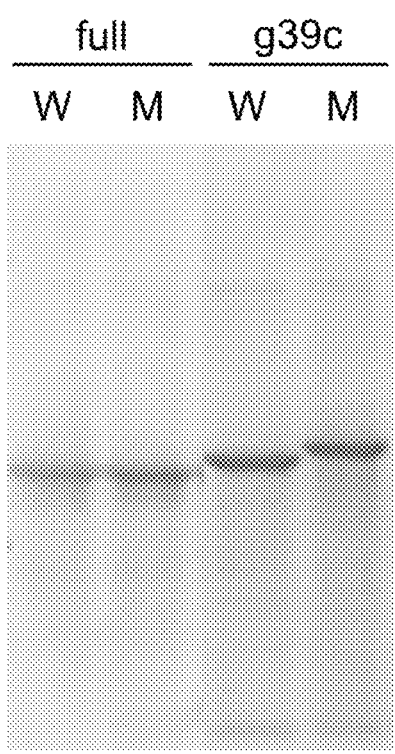
FIG. 7 shows a result obtained by detecting, through polyacrylamide gel electrophoresis as a molecular sieve, mutant-type KRas gene by using the KRas gene clamping probe. In this figure, "full" corresponds to a full match-type clamping probe, and "g39c" corresponds to a g39c clamping probe. Besides, "W" corresponds to WT-70(g34t) oligonucleotide, and "M" corresponds to MT-70 oligonucleotide.

Results are shown in FIG. 7. When the full match-type clamping probe was added, there was no difference in the mobility between WT-70 and MT-70(g34t), but when the g39c clamping probe was added, there arose a definitely difference. These results suggest that the wild-type KRas gene and the mutant-type KRas gene can be distinguished from each other at normal temperature merely via the polyacrylamide gel electrophoresis if the clamping probe of the present invention is used, specifically, the clamping probe having weaker binding force to a target nucleic acid molecule than full match-type clamping such as mismatch-type clamping is used.

Example 4: Detection of Mutant-Type KRas Gene Using Parallel-Type and Diamond-Type Clamping Probes (Purpose)

The clamping probe is classified into two types of the parallel-type and the diamond-type, and it was verified that the clamping probe of either type can detect mutant-type KRas gene by the nucleic acid amplification method.

(Method)

The basic operation was performed in the same manner as in Examples 1 and 2. As the parallel-type, the clamping probe consisting of the nucleotide sequence represented by SEQ ID NO:5 prepared in Example 1 was used. Besides, as the diamond-type, a clamping probe consisting of a nucleotide sequence represented by SEQ ID NO: 15 was used. Both the clamping probes are full match-type clamping probes completely complementary to the wild-type KRas gene.

(Results)

Figure 8A:
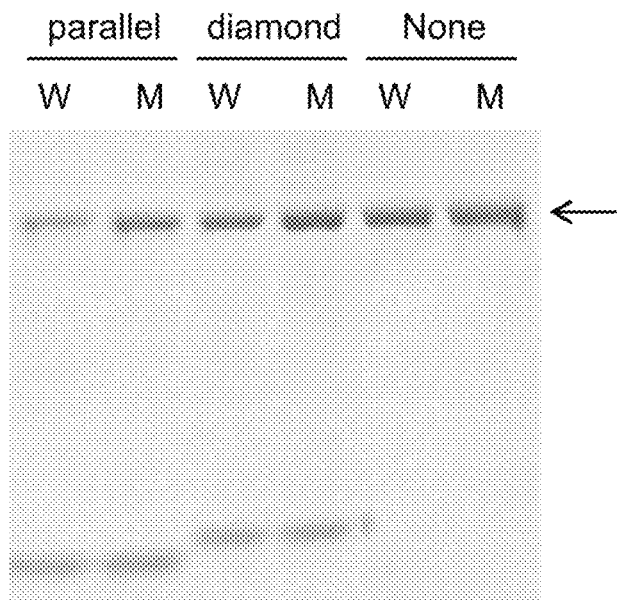
FIG. 8A shows a result of polyacrylamide gel electrophoresis of the amplified product obtained by using each of the clamping probes. "None" shows a result obtained without using a clamping probe. In this figure, an arrow points to the amplified products in a detection region.
Figure 8B:
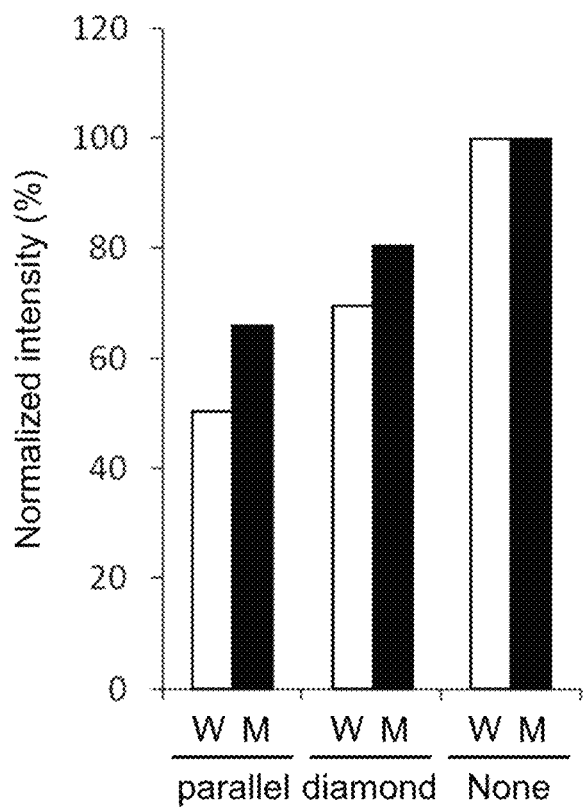
FIG. 8B is a diagram obtained by graphing out, using Image-J, bands pointed to by the arrow in FIG. 8A.

Results are shown in FIG. 8. It was proved that both the parallel-type clamping probe and the diamond-type clamping probe inhibit the amplification of the wild-type KRas gene. Besides, it was revealed that the parallel-type clamping probe has a stronger inhibition effect for the wild-type gene than the diamond-type clamping probe.

Example 5: Binding Force of Clamping Probe Obtained Via Melting Curve Analysis (Purpose)

The binding force between the clamping probe and the KRas gene, that is, the target nucleic acid molecule, was verified via melting curve analysis.

(Method)

In the same manner as in Example 2, the KRas gene derived from the HEK293 cell was used as the wild-type KRas gene, and the KRas gene derived from the MIAPaCa-2 cell was used as the G12C mutant-type KRAS gene.

Besides, as the clamping probes, the full match-type clamping probe consisting of the nucleotide sequence represented by SEQ ID NO: 5 and the mismatch-type a36t clamping probe consisting of the nucleotide sequence represented by SEQ ID NO: 8 prepared in Example 1 were used.

After causing 10 pmol of each clamping probe to bind to 10 pmol of wild-type KRas gene or the G12C mutant-type KRas gene by annealing in the presence of SYBR Gold, the resultant was subjected to the melting curve analysis by increasing the temperature from 25° C. to 95° C.

(Results)

Figure 9A:
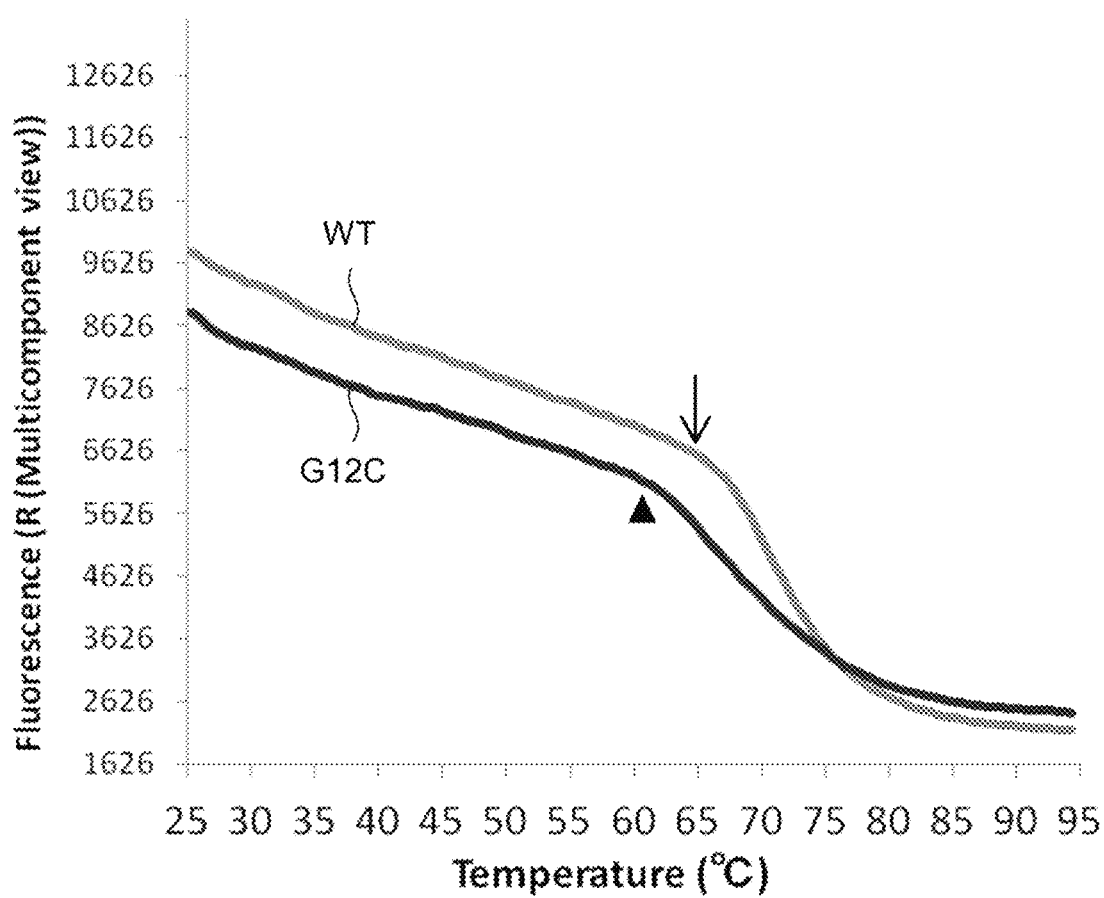
FIG. 9A shows results obtained by using a full match-type clamping probe.
Figure 9B:
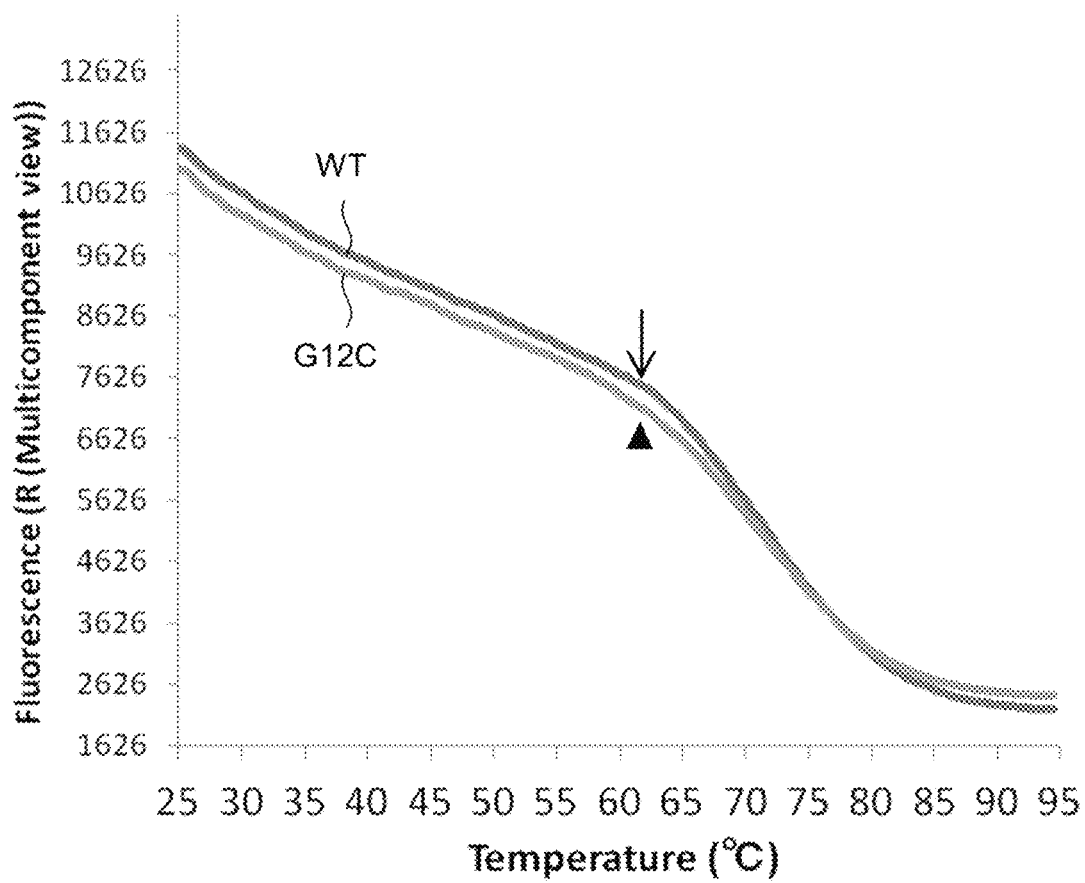
FIG. 9B shows results obtained by using a mismatch-type a36t clamping probe. In this figure, "WT" corresponds to wild-type KRas gene, "G12C" corresponds to mutant-type KRas gene, and an arrow and an arrowhead point to dissociation start points of the genes, respectively.

Results are shown in FIG. 9. FIGS. 9A and 9B illustrate melting curves obtained respectively by using the full match-type clamping probe and the a36t clamping probe. In using the full match-type clamping probe, bond dissociation from the G12C mutant-type KRas started in the vicinity of 60° C. (an arrowhead). The bond dissociation from the wild-type KRas gene started, however, in the vicinity of 65° C. higher by 5° C. On the other hand, in using the mismatch-type a36t clamping probe, dissociation from the wild-type KRas gene and the G12c mutant-type KRas gene both started around 62° C., and thus, there was no difference therebetween.

Besides, it was revealed that in using either of the clamping probes, the bond dissociation between the clamping probe and the KRas gene was caused at 72° C., which is employed as a DNA extension temperature in usual PCR.

Example 6: Detection of KRas Gene Mutation Using Shuttle PCR (Purpose)

It was suggested, on the basis of the results of Example 5, that the bond between the clamping probe and the KRas gene is not obtained or is very weak at the extension temperature of 72° C. in the PCR. Therefore, shuttle PCR not including the extension reaction at 72° C. was performed so as to verify whether or not the clamping probe of the present invention can exhibit its original ability of inhibiting the amplification of the wild-type gene.

(Method)

Wild-type and mutant-type KRas genes and a full match-type clamping probe used here were the same as those used in Example 5.

In the coexistence of 10 pmol of the full match-type clamping probe consisting of the nucleotide sequence represented by SEQ ID NO: 5 prepared in Example 1, the shuttle PCR was performed with 10 ng of the wild-type or mutant-type KRas gene used as a template. A reaction solution of each sample for the shuttle PCR was prepared as follows: Two (2) µL of 10× Paq 5000 Reaction Buffer, 1.6 µL of 2.5 mM dNTP, 0.2 µL (2 pmol) of 10 µM Right primer, 0.2 µL (2 pmol) of 10 µM Left primer, 0.2 µL of Paq 5000 DNA Polymerase, 1 µL (10 pmol) of 10 µL probe, 1 µL of template KRas gene and sterile water in an amount for attaining a total amount of 20 µL were mixed. Subsequently, a thermal cycler was used to perform the denaturation at 98° C. for 2 minutes, and then the PCR reaction was performed for 30 cycles of 98° C. for 20 seconds and each annealing temperature of 60 seconds. The annealing temperatures were set to 50.0° C., 51.5° C., 52.6° C., 54.0° C., 55.7° C., 57.1° C., 58.2° C. and 60.0° C. by using a gradient function of the thermal cycler.

(Results)

Figure 10A:
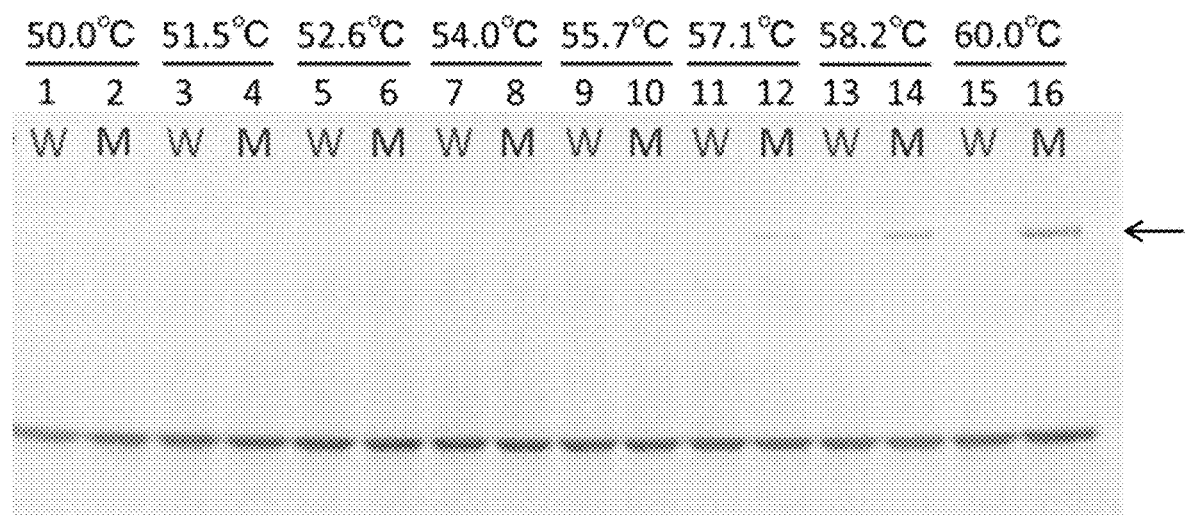
FIG. 10A is a diagram obtained by visualizing, with a non-denaturing gel, the amplified product obtained at each annealing temperature. In the figure, an arrow points to a position of the amplified product.
Figure 10B:
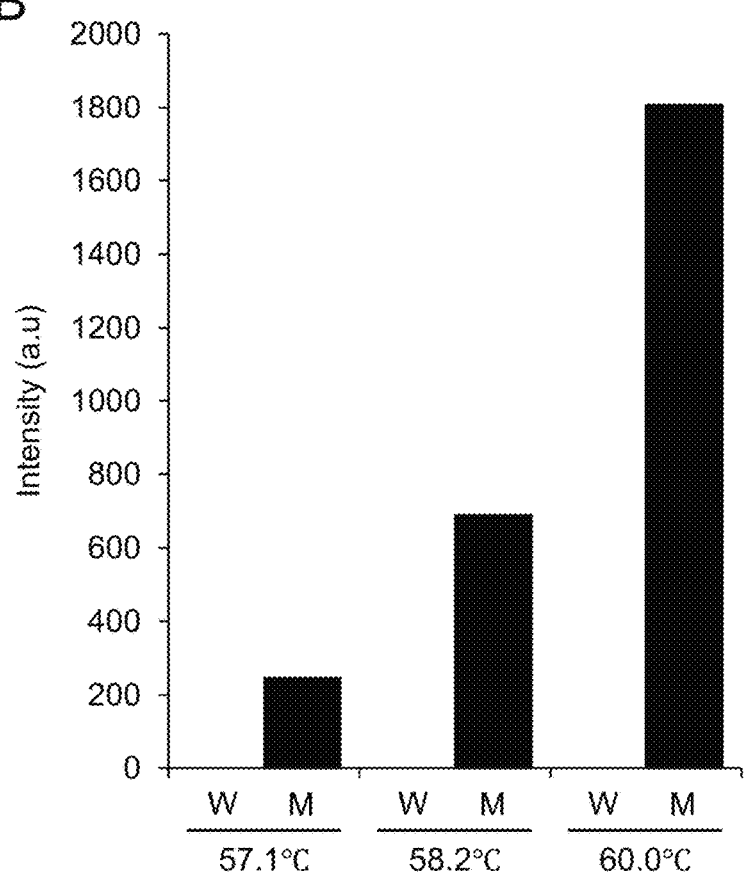
FIG. 10B is a graph obtained by graphing out, using Image-J, bands pointed to by the arrow obtained at some of the annealing temperatures of FIG. 10A (57.1° C., 58.2° C. and 60.0° C.).

Results are shown in FIG. 10. It was revealed that the amplification of the wild-type KRas gene can be completely inhibited at least up to 60° C. when the full match-type clamping probe having strong binding force is used. In other words, it was revealed that the ability of inhibiting the amplification of the wild-type gene can be enhanced, as expected, by employing the shuttle PCR with the annealing temperature set to be lower than usual 72° C.

Example 7: Detection of KRas Gene Mutation in Using Other Primers (Purpose)

Up to Example 6, the KRas F & R primer pair represented by SEQ ID NOS: 1 and 12 was used for detecting the KRas gene mutation. In using this primer pair, however, the amplification reaction did not sufficiently proceed at 65° C. or higher due to the dissociation.

Therefore, a novel primer pair whose base lengths were increased to increase the Tm value was used to verify detection accuracy for the KRas gene mutation.

(Method)

The novel primer pair KRas-sense68 (SEQ ID NO: 16) and KRas-anti68 (SEQ ID NO: 17) was designed so that the PCR could be performed even at a high temperature. As the clamping probe, the full match-type clamping probe consisting of the nucleotide sequence represented by SEQ ID NO: 5 prepared in Example 1 was used.

The conditions for the PCR were in accordance with those of the method of the shuttle PCR of Example 6. The annealing temperatures were set to 56.0° C. (lane 1), 58.9° C. (lane 2), 61.0° C. (lane 3), 63.5° C. (lane 4), 65.7° C. (lane 5), 67.4° C. (lane 6), 68.0° C. (lane 7) and 70.0° C. (lane 8). After the reaction, the amplified product was separated by the non-denaturing gel electrophoresis to be visualized.

(Results)

Figure 11A:
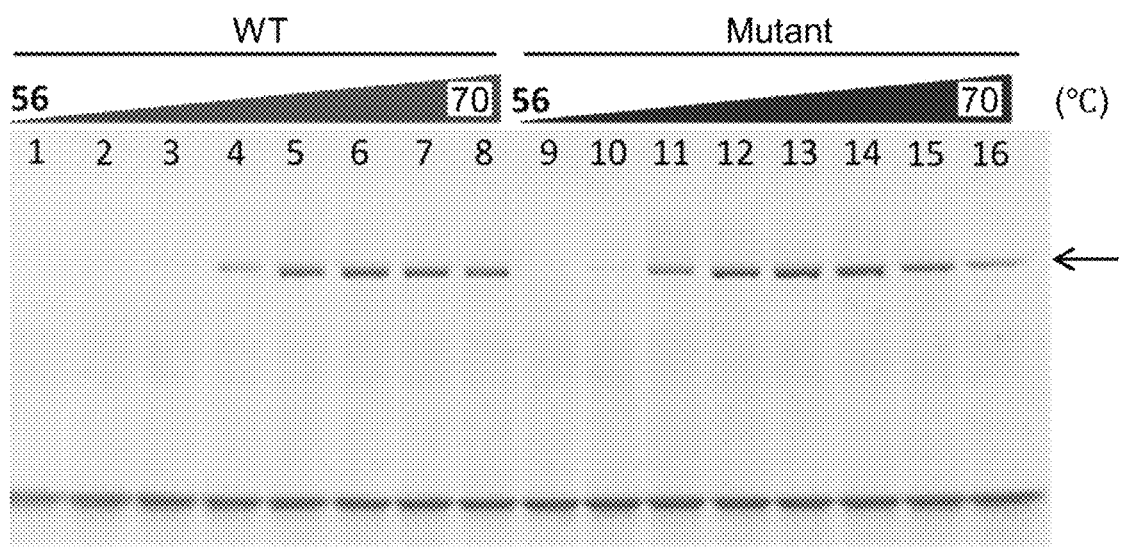
FIG. 11A is a diagram obtained by visualizing, with a non-denaturing gel, the amplified product obtained at each annealing temperature. In the figure, an arrow points to a position of the amplified product.
Figure 11B:
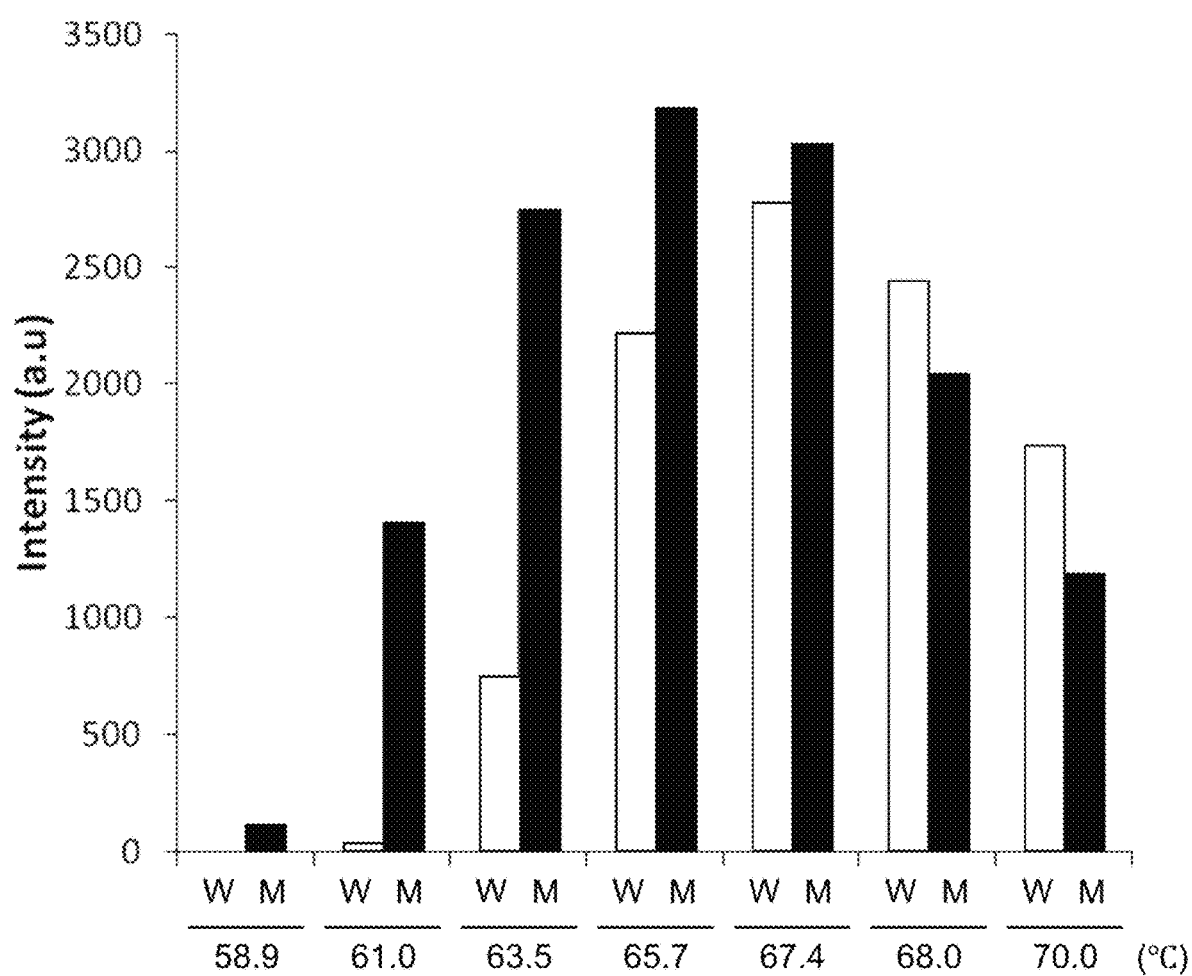
FIG. 11B is a graph obtained by graphing out, using Image-J, bands pointed to by the arrow obtained at each annealing temperature of FIG. 11A.

Results are shown in FIG. 11. When the Tm value of the primer pair was increased, the amplification could be performed even at an annealing temperature of 61° C. or higher. Accordingly, it was revealed that the detection of the KRas mutation using the clamping probe of the present invention can be performed even at a high temperature if the Tm value of the primers is changed. If the annealing temperature was 61° C. or higher, however, the wild-type KRas gene was also gradually amplified, and at the annealing temperature of 68° C., the amounts of the amplified products of the wild-type and mutant-type KRas genes were reversed. Accordingly, it was revealed that the annealing temperature lower than 68° C. is preferred even if the Tm value of the primers is increased.

Example 8: Detection of KRas Gene Mutation in the Presence of Wild-Type KRas Gene (Purpose)

Up to Example 7, the clamping probe of the present invention was evaluated on the assumption that the wild-type or mutant-type KRas gene was singly present. Therefore, in this example, in order to verify whether or not the clamping probe of the present invention is applicable as an actual clinical reagent, the KRas gene mutation was detected in the mixed presence of the wild-type and mutant-type KRas genes.

(Method)

The wild-type and mutant-type KRas genes were mixed in a ratio of 1:1 (7.5 ng:7.5 ng), 10:1 (75 ng:7.5 ng) and 20:1 (150 ng:7.5 ng), and each of the resultant mixtures was subjected to the shuttle PCR in the same manner as in Example 6 in the coexistence of 10 pmol of the full match-type clamping probe consisting of the nucleotide sequence represented by SEQ ID NO: 5 prepared in Example 1. The annealing temperature was set to 60° C.

Each of the thus obtained amplified products was used for performing 3-step PCR using Taq polymerase. A reaction solution of each sample for the 3-step PCR was prepared as follows: Two (2) µL of 10× ThermoPol Reaction Buffer, 1.6 µL of 2.5 mM dNTP, 0.2 µL (2 pmol) of 10 µM KRAS Right primer, 0.2 µL (2 pmol) of 10 µM KRAS Left primer, 0.1 µL of Taq DNA Polymerase, 1 µL (10 pmol) of 10 µM probe, 1 µL of each amplified product and sterile water in an amount for attaining a total amount of 20 µL were mixed. Subsequently, a thermal cycler was used to perform the denaturation at 98° C. for 2 minutes, and then the PCR reaction was performed for 30 cycles each of 98° C. for 20 seconds, 55° C. for 20 seconds and 72° C. for 10 seconds, and the resultant was ultimately allowed to stand at 72° C. for 5 minutes. The thus obtained amplified product was purified using PCR clean up kits (Clonetech). Then, 6.5 µL of the purified PCR product was subjected to nucleotide sequence determination by a usual method using BigDye Terminator v3.1 cycle sequencing kit (Thermo Fisher Scientific).

(Results)

Figure 12A:
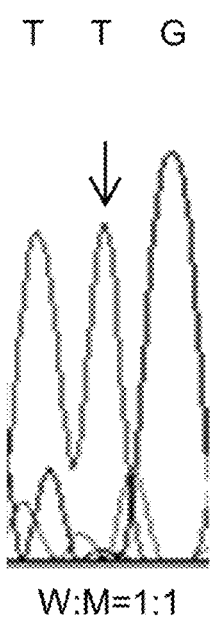
FIG. 12 show a part of a nucleotide sequence containing a mutation site obtained in an amplified product in detecting KRas gene mutation using the clamping probe of the present invention in the mixed presence of wild-type (W) and mutant-type (M) KRas genes. A mixing ratio between the wild-type KRas gene and the mutant-type KRas gene is 1:1 in FIG. 12A, 10:1 in FIG. 12B and 20:1 in FIG. 12C. The three bases in the figure are TGG in the wild-type KRas gene and TTG in the mutant-type KRas gene.
Figure 12B:
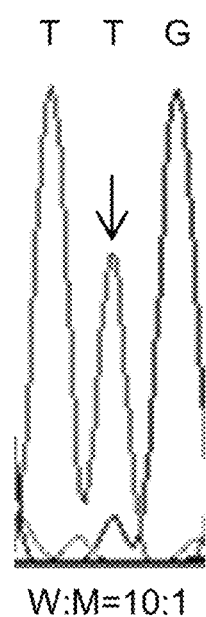
Figure 12C:
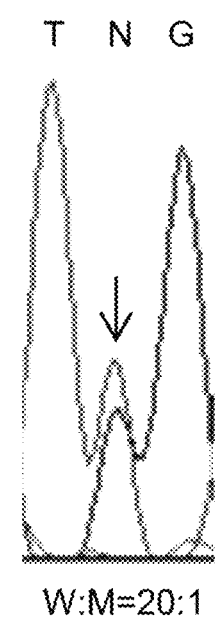

Results are shown in FIG. 12. When the mixing ratio between the wild-type and mutant-type KRas genes was 1:1 or 10:1, the nucleotide sequence of the mutant-type KRas gene, that is, TTG, alone was detected, and the nucleotide sequence of the wild-type KRas gene, that is, TGG, was substantially completely inhibited (FIGS. 12A and 12B). On the other hand, when the mixing ratio was 20:1, the wild-type KRas gene was rather amplified, but the amount of the mutant-type KRas gene was found to be still larger (FIG. 12C). These results reveal that a wild-type and mutant-type target nucleic acid molecules can be distinguished from each other to selectively amplify the mutant-type target nucleic acid molecule alone by using a non-modified DNA probe having different binding force like a full match-type clamping probe. Besides, it was revealed that the mutant-type target nucleic acid molecule can be sufficiently detected even if the wild-type target nucleic acid molecule is mixedly present as long as the amount of the mutant-type target nucleic acid molecule is 1/20 or more.

Besides, these results reveal that the clamping probe of the present invention can be used also in the well-known known mutation site determination method such as the invader method.

It is noted that all the publications, patents and patent applications cited herein are incorporated herein by reference.

We claim:

1. A clamping probe for use for detecting a known mutation in a target nucleic acid molecule caused by substitution, deletion or addition of one or several bases, the clamping probe comprising a single-stranded nucleic acid molecule comprising a first target nucleic acid complementary region, a second target nucleic acid complementary region, a hairpin region and a double-stranded region, either (i) a 3'-end of the first target nucleic acid complementary region and a 5'-end of the second target nucleic acid complementary region being connected to the hairpin region and a 3'-end of the second target nucleic acid complementary region and a 5'-end of the first target nucleic acid complementary region being connected to the double-stranded region, or (ii) a 3'-end of the second target nucleic acid complementary region and a 5'-end of the first target complementary region being connected to the hairpin region and a 3'-end of the first target nucleic acid complementary region and a 5'-end of the second target nucleic acid complementary region being connected to the double-stranded region, wherein the first target complementary region consists of a nucleotide sequence complementary to a nucleotide sequence of a first target nucleic acid region, the first target nucleic acid region consists of continuous 15 to 30 bases including a site of the known mutation in a wild-type target nucleic acid molecule, the second target nucleic acid complementary region consists of a nucleotide sequence complementary to a nucleotide sequence of a second target nucleic acid region, the second target nucleic acid region consists of 15 to 30 bases flanking on a 5'-end side or a 3'-end side of the first target nucleic acid region in the target nucleic acid molecule, the hairpin region comprises: a double-stranded moiety consisting of mutually complementary nucleotide sequences each of 3 to 10 bases; and a single-stranded moiety consisting of a nucleotide sequence of 3 to 10 bases linking any combination of a 5'-end and a 3'-end of the double-stranded moiety, and the double-stranded region consists of mutually complementary nucleotide sequences each of 3 to 10 bases.

2. The clamping probe according to claim 1, wherein the first target nucleic acid complementary region comprises a mismatch site of 1 to 3 bases, wherein the first target nucleic acid complementary region is not complementary to the nucleotide sequence of the first target nucleic acid region at the mismatch site.

3. The clamping probe according to claim 1, comprising a spacer region consisting of a nucleotide sequence of 1 to 5 bases linking the first target nucleic acid complementary region and/or the second target nucleic acid complementary region to the hairpin region, and/or the first target nucleic acid complementary region and/or the second target nucleic acid complementary region to the double-stranded region.

4. The clamping probe according to claim 1, wherein a G-quartet region is connected to at least one of a free 5'-end and a free 3'-end of the double-stranded region.

5. The clamping probe according to claim 1, wherein the target nucleic acid molecule is KRas gene represented by SEQ ID NO: 1.

6. The clamping probe according to claim 5, wherein the mutation is substitution mutation in at least one base selected from the group consisting of positions 34, 35 and 38.

7. The clamping probe according to claim 1, wherein the target nucleic acid molecule is EGFR gene represented by SEQ ID NO: 2.

8. The clamping probe according to claim 7, wherein the mutation is substitution mutation in any one of a base selected from the group consisting of positions 2115, 2573 and 2582.

9. A method for detecting presence of a known mutation in a target nucleic acid molecule, comprising:
　mixing a nucleic acid sample comprising the target nucleic acid molecule with the clamping probe according to claim 1 for binding the target nucleic acid molecule and the clamping probe to each other; and
　detecting the mutation in the target nucleic acid molecule based on a difference in binding force between the target nucleic acid molecule and the clamping probe caused by the presence of the mutation in the target nucleic acid molecule;
　wherein detection based on the difference in the binding force is
　(a) detection based on an amount difference of an amplified product obtained by a nucleic acid amplification method, and a region of the target nucleic acid molecule comprising the first target nucleic acid region and the second target nucleic acid region is amplified by the nucleic acid amplification method; or
　(b) detection using a molecular sieve.

10. The method according to claim 9, wherein the target nucleic acid molecule is KRas gene represented by SEQ ID NO: 1.

11. The method according to claim 10, wherein the mutation is substitution mutation in at least one base selected from the group consisting of position 34, position 35 and position 38.

12. The method according to claim 9, wherein the target nucleic acid molecule is EGFR gene represented by SEQ ID NO: 2.

13. The method according to claim 12, wherein the mutation is substitution mutation in any one base selected from the group consisting of position 2115, position 2573 and position 2582.

14. A method for determining whether a subject is affected with colorectal cancer, comprising:
　preparing a nucleic acid sample from a biological sample obtained from the subject;
　detecting presence of a known mutation in the KRas gene represented by SEQ ID NO:1 by:
　　mixing a nucleic acid sample comprising the KRas gene with the clamping probe according to claim 1 for binding the KRas gene and the clamping probe to each other; and
　　detecting the mutation in the KRas gene based on a difference in binding force between the KRas gene and the clamping probe caused by the presence of the mutation in the KRas gene; and
　determining that the subject is affected with colorectal cancer if the KRas gene having the mutation is detected in the nucleic acid sample.

15. A method for determining whether a subject is affected with non-small cell lung cancer, comprising:
　preparing a nucleic acid sample from a biological sample obtained from the subject;
　detecting presence of a known mutation in the EGFR gene represented by SEQ ID NO:2 by:
　　mixing a nucleic acid sample comprising the EGFR gene with the clamping probe according to claim 1 for binding the EGFR gene and the clamping probe to each other; and
　　detecting the mutation in the EGFR gene based on a difference in binding force between the EGFR gene and the clamping probe caused by the presence of the mutation in the EGFR gene; and
　determining that the subject is affected with non-small cell lung cancer if the EGFR gene having mutation is detected in the nucleic acid sample.

16. A method for determining whether a subject is affected with colorectal cancer, comprising:
　preparing a nucleic acid sample from a biological sample obtained from the subject;
　detecting presence of a known mutation in the KRas gene represented by SEQ ID NO:1 by:
　　mixing a nucleic acid sample comprising the KRas gene with the clamping probe according to claim 1 for binding the KRas gene and the clamping probe to each other; and
　　detecting the mutation in the KRas gene based on a difference in binding force between the KRas gene and the clamping probe caused by the presence of the mutation in the KRas gene; and
　determining that the subject is affected with colorectal cancer if the KRas gene having the mutation is detected in the nucleic acid sample,
　wherein the mutation is substitution mutation in at least one base selected from the group consisting of position 34, position 35 and position 38.

17. A method for determining whether a subject is affected with non-small cell lung cancer, comprising:
　preparing a nucleic acid sample from a biological sample obtained from the subject;
　detecting presence of a known mutation in the EGFR gene represented by SEQ ID NO:2 by:
　　mixing a nucleic acid sample comprising the EGFR gene with the clamping probe according to claim 1 for binding the EGFR gene and the clamping probe to each other; and
　　detecting the mutation in the EGFR gene based on a difference in binding force between the EGFR gene and the clamping probe caused by the presence of the mutation in the EGFR gene; and
　determining that the subject is affected with non-small cell lung cancer if the EGFR gene having mutation is detected in the nucleic acid sample,
　wherein the mutation is substitution mutation in any one base selected from the group consisting of position 2115, position 2573 and position 2582.

* * * * *

SEQUENCE LISTING

<160> NUMBER OF SEQ ID NOS: 17

<210> SEQ ID NO 1
<211> LENGTH: 567
<212> TYPE: DNA
<213> ORGANISM: Homo sapiens
<220> FEATURE:
<223> OTHER INFORMATION: KRAS gene

<400> SEQUENCE: 1

```
atgactgaat ataaacttgt ggtagttgga gctggtggcg taggcaagag tgccttgacg    60
atacagctaa ttcagaatca ttttgtggac gaatatgatc aacaataga ggattcctac   120
aggaagcaag tagtaattga tggagaaacc tgtctcttgg atattctcga cacagcaggt   180
caagaggagt acagtgcaat gagggaccag tacatgagga ctgggagggg ctttctttgt   240
gtatttgcca taaataatac taaatcattt gaagatattc accattatag agaacaaatt   300
aaaagagtta aggactctga agatgtacct atggtcctag taggaaataa atgtgatttg   360
ccttctagaa cagtagacac aaaacaggct caggacttag caagaagtta tggaattcct   420
tttattgaaa catcagcaaa gacaagacag gtgttgatg atgccttcta tacattagtt   480
cgagaaattc gaaaacataa agaaaagatg agcaaagatg gtaaaagaa gaaaagaag   540
tcaaagacaa agtgtgtaat tatgtaa                                      567
```

<210> SEQ ID NO 2
<211> LENGTH: 3633
<212> TYPE: DNA
<213> ORGANISM: Homo sapiens
<220> FEATURE:
<223> OTHER INFORMATION: EGFR gene

<400> SEQUENCE: 2

```
atgcgaccct ccgggacggc cggggcagcg ctcctggcgc tgctggctgc gctctgcccg    60
gcgagtcggg ctctggagga aaagaaagtt tgccaaggca cgagtaacaa gctcacgcag   120
ttgggcactt ttgaagatca ttttctcagc ctccagagga tgttcaataa ctgtgaggtg   180
gtccttggga atttggaaat tacctatgtg cagaggaatt atgatctttc cttcttaaag   240
accatccagg aggtggctgg ttatgtcctc attgccctca acacagtgga gcgaattcct   300
ttggaaaacc tgcagatcat cagaggaaat atgtactacg aaaattccta tgccttagca   360
gtcttatcta actatgatgc aaataaaacc ggactgaagg agctgcccat gagaaattta   420
caggaaatcc tgcatggcgc cgtgcggttc agcaacaacc ctgccctgtg caacgtggag   480
agcatccagt ggcgggacat agtcagcagt gactttctca gcaacatgtc gatggacttc   540
cagaaccacc tgggcagctg ccaaaagtgt gatccaagct gtcccaatgg gagctgctgg   600
ggtgcaggag aggagaactg ccagaaactg accaaaatca tctgtgccca gcagtgctcc   660
gggcgctgcc gtggcaagtc ccccagtgac tgctgccaca accagtgtgc tgcaggctgc   720
acaggccccc gggagagcga ctgcctggtc tgccgcaaat tccgagacga agccacgtgc   780
aaggacacct gccccccact catgctctac aaccccacca cgtaccagat ggatgtgaac   840
cccgagggca atacagcttt ggtgccacc tgcgtgaaga gtgtccccg taattatgtg   900
gtgacagatc acggctcgtg cgtccgagcc tgtggggccg acagctatga gatggaggaa   960
gacggcgtcc gcaagtgtaa gaagtgcgaa gggccttgcc gcaaagtgtg taacggaata  1020
ggtattggtg aatttaaaga ctcactctcc ataaatgcta cgaatattaa acacttcaaa  1080
aactgcacct ccatcagtgg cgatctccac atcctgccgg tggcatttag ggtgactccc  1140
```

```
ttcacacata ctcctcctct ggatccacag gaactggata ttctgaaaac cgtaaaggaa    1200
atcacagggt ttttgctgat tcaggcttgg cctgaaaaca ggacggacct ccatgccttt    1260
gagaacctag aaatcatacg cggcaggacc aagcaacatg gtcagttttc tcttgcagtc    1320
gtcagcctga acataacatc cttgggatta cgctccctca aggagataag tgatggagat    1380
gtgataattt caggaaacaa aaatttgtgc tatgcaaata caataaactg gaaaaaactg    1440
tttgggacct ccgtcagaa aaccaaaatt ataagcaaca gaggtgaaaa cagctgcaag     1500
gccacaggcc aggtctgcca tgccttgtgc tcccccgagg gctgctgggg cccggagccc    1560
agggactgcg tctcttgccg gaatgtcagc cgaggcaggg aatgcgtgga caagtgcaag    1620
cttctggagg gtgagccaag ggagtttgtg gagaactctg agtgcataca gtgccaccca    1680
gagtgcctgc ctcaggccat gaacatcacc tgcacaggac ggggaccaga caactgtatc    1740
cagtgtgccc actacattga cggcccccac tgcgtcaaga cctgcccggc aggagtcatg    1800
ggagaaaaca cacccctggt ctggaagtac gcagacgccg ccatgtgtg ccacctgtgc     1860 catccaaact gcacctacgg atgcactggg ccaggtcttg aaggctgtcc aacgaatggg    1920
cctaagatcc cgtccatcgc cactgggatg gtggggccc tcctcttgct gctggtggtg     1980
gccctgggga tcggcctctt catgcgaagg cgccacatcg ttcggaagcg cacgctgcgg    2040
aggctgctgc aggagaggga gcttgtggag cctcttacac ccagtggaga agctcccaac    2100
caagctctct tgaggatctt gaaggaaact gaattcaaaa agatcaaagt gctgggctcc    2160
ggtgcgttcg gcacggtgta taagggactc tggatcccag aaggtgagaa agttaaaatt    2220
cccgtcgcta tcaaggaatt aagagaagca acatctccga aagccaacaa ggaaatcctc    2280
gatgaagcct acgtgatggc cagcgtggac aaccccacg tgtgccgcct gctgggcatc     2340
tgcctcacct ccaccgtgca actcatcacg cagctcatgc ccttcggctg cctcctggac    2400
tatgtccggg aacacaaaga caatattggc tcccagtacc tgctcaactg gtgtgtgcag    2460
atcgcaaagg gcatgaacta cttggaggac cgtcgcttgg tgcaccgcga cctggcagcc    2520
aggaacgtac tggtgaaaac accgcagcat gtcaagatca cagattttgg gctggccaaa    2580
ctgctgggtg cggaagagaa agaataccat gcagaaggag gcaaagtgcc tatcaagtgg    2640
atggcattgg aatcaatttt acacagaatc tatacccacc agagtgatgt ctggagctac    2700
ggggtgaccg tttgggagtt gatgaccttt ggatccaagc catatgacgg aatccctgcc    2760
agcgagatct cctccatcct ggagaaagga gaacgcctcc ctcagccacc catatgtacc    2820
atcgatgtct acatgatcat ggtcaagtgc tggatgatag acgcagatag tcgcccaaag    2880
ttccgtgagt tgatcatcga attctccaaa atggcccgag accccagcg ctaccttgtc     2940 attcaggggg atgaaagaat gcatttgcca agtcctacag actccaactt ctaccgtgcc    3000
ctgatggatg aagaagacat ggacgacgtg gtggatgccg acgagtacct catcccacag    3060
cagggcttct tcagcagccc ctccacgtca cggactcccc tcctgagctc tctgagtgca    3120
accagcaaca attccaccgt ggcttgcatt gatagaaatg ggctgcaaag ctgtcccatc    3180
aaggaagaca gcttcttgca gcgatacagc tcagaccccca caggcgcctt gactgaggac    3240
agcatagacg acaccttcct cccagtgcct gaatacataa accagtccgt tcccaaaagg    3300
cccgctggct ctgtgcagaa tcctgtctat cacaatcagc ctctgaaccc cgcgcccagc    3360
agagacccac actaccagga cccccacagc actgcagtgg caaccccga gtatctcaac     3420 actgtccagc ccacctgtgt caacagcaca ttcgacagcc ctgcccactg ggcccagaaa    3480
```
ggcagccacc aaattagcct ggacaaccct gactaccagc aggacttctt tcccaaggaa    3540
gccaagccaa atggcatctt taagggctcc acagctgaaa atgcagaata cctaagggtc    3600
gcgccacaaa gcagtgaatt tattggagca tga    3633

<210> SEQ ID NO 3
<211> LENGTH: 15
<212> TYPE: DNA
<213> ORGANISM: Artificial
<220> FEATURE:
<223> OTHER INFORMATION: synthetic

<400> SEQUENCE: 3
ggttggtgtg gttgg    15

<210> SEQ ID NO 4
<211> LENGTH: 13
<212> TYPE: DNA
<213> ORGANISM: Artificial
<220> FEATURE:
<223> OTHER INFORMATION: synthetic

<400> SEQUENCE: 4
ggagggaacc tcc    13

<210> SEQ ID NO 5
<211> LENGTH: 65
<212> TYPE: DNA
<213> ORGANISM: Artificial
<220> FEATURE:
<223> OTHER INFORMATION: WT-KRas-clumping probe

<400> SEQUENCE: 5
ggagggtacg ccaccagctc aactaggag ggaacctcca caagtttata ttcagtcatc    60
cctcc    65

<210> SEQ ID NO 6
<211> LENGTH: 65
<212> TYPE: DNA
<213> ORGANISM: Artificial
<220> FEATURE:
<223> OTHER INFORMATION: a27c-KRas-clumping probe

<400> SEQUENCE: 6
ggagggtacg ccaccagctc ccactaggag ggaacctcca caagtttata ttcagtcatc    60
cctcc    65

<210> SEQ ID NO 7
<211> LENGTH: 65
<212> TYPE: DNA
<213> ORGANISM: Artificial
<220> FEATURE:
<223> OTHER INFORMATION: a33c-KRas-clumping probe

<400> SEQUENCE: 7
ggagggtacg ccacccgctc caactaggag ggaacctcca caagtttata ttcagtcatc    60
cctcc    65

<210> SEQ ID NO 8
<211> LENGTH: 65
<212> TYPE: DNA
<213> ORGANISM: Artificial
<220> FEATURE:
<223> OTHER INFORMATION: a36t-KRas-clumping probe

<400> SEQUENCE: 8
ggagggtacg cctccagctc aactaggag ggaacctcca caagtttata ttcagtcatc    60
cctcc    65

<210> SEQ ID NO 9
<211> LENGTH: 65
<212> TYPE: DNA
<213> ORGANISM: Artificial
<220> FEATURE:
<223> OTHER INFORMATION: c37g-KRas-clumping probe

<400> SEQUENCE: 9
ggagggtacg cgaccagctc caactaggag ggaacctcca caagtttata ttcagtcatc    60
cctcc    65

<210> SEQ ID NO 10
<211> LENGTH: 65
<212> TYPE: DNA
<213> ORGANISM: Artificial
<220> FEATURE:
<223> OTHER INFORMATION: g39c-KRas-clumping probe

<400> SEQUENCE: 10
ggagggtacc ccaccagctc caactaggag ggaacctcca caagtttata ttcagtcatc    60
cctcc    65

<210> SEQ ID NO 11
<211> LENGTH: 30
<212> TYPE: DNA
<213> ORGANISM: Artificial
<220> FEATURE:
<223> OTHER INFORMATION: primer

<400> SEQUENCE: 11
atttgatagt gtattaacct tatgtgtgac    30

<210> SEQ ID NO 12
<211> LENGTH: 24
<212> TYPE: DNA
<213> ORGANISM: Artificial
<220> FEATURE:
<223> OTHER INFORMATION: primer

<400> SEQUENCE: 12
acctctattg ttggatcata ttcg    24

<210> SEQ ID NO 13
<211> LENGTH: 70
<212> TYPE: DNA
<213> ORGANISM: Artificial
<220> FEATURE:
<223> OTHER INFORMATION: synthetic

<400> SEQUENCE: 13
atgactgaat ataaacttgt ggtagttgga gctggtggcg taggcaagag tgccttgacg    60
atacagctaa    70

<210> SEQ ID NO 14
<211> LENGTH: 70
<212> TYPE: DNA
<213> ORGANISM: Artificial
<220> FEATURE:

```
<223> OTHER INFORMATION: synthetic

<400> SEQUENCE: 14
atgactgaat ataaacttgt ggtagttgga gcttgtggcg taggcaagag tgccttgacg    60
atacagctaa                                                           70

<210> SEQ ID NO 15
<211> LENGTH: 65
<212> TYPE: DNA
<213> ORGANISM: Artificial
<220> FEATURE:
<223> OTHER INFORMATION: WT-KRas-clumping probe

<400> SEQUENCE: 15
ggagggtacc acaagtttat attcagggag ggaacctcct gcctacgcca ccagctccac    60
cctcc                                                                65

<210> SEQ ID NO 16
<211> LENGTH: 39
<212> TYPE: DNA
<213> ORGANISM: Artificial
<220> FEATURE:
<223> OTHER INFORMATION: primer

<400> SEQUENCE: 16
tggtggagta tttgatagtg tattaacctt atgtgtgac                           39

<210> SEQ ID NO 17
<211> LENGTH: 43
<212> TYPE: DNA
<213> ORGANISM: Artificial
<220> FEATURE:
<223> OTHER INFORMATION: primer

<400> SEQUENCE: 17
gcatattaaa acaagattta cctctattgt tggatcatat tcg                      43
```